United States Patent [19]

Inoue et al.

[11] Patent Number: 4,552,894
[45] Date of Patent: Nov. 12, 1985

[54] 2-FLUOROETHOXY-SUBSTITUTED BENZENE DERIVATIVES

[75] Inventors: Tsuneo Inoue, Yokohama; Kiyoshi Nakatani, Tokyo; Kengo Oda; Tutomu Ishii, both of Yokohama; Takatoshi Udagawa, Chigasaki; Shiro Shiraishi, Kamakura, all of Japan

[73] Assignee: Mitsui Toatsu Chemicals, Inc., Tokyo, Japan

[21] Appl. No.: 573,472

[22] Filed: Jan. 24, 1984

[30] Foreign Application Priority Data

Jan. 25, 1983 [JP] Japan .................................. 58-9396
Jan. 26, 1983 [JP] Japan .................................. 58-9969

[51] Int. Cl.⁴ ............... A01N 43/16; C07C 51/36; C07D 317/44
[52] U.S. Cl. .................. 514/464; 549/437; 549/445; 568/592; 568/609
[58] Field of Search ............ 549/437, 445; 568/592, 568/609; 514/464

[56] References Cited

U.S. PATENT DOCUMENTS 3,709,914  1/1973  Siddall .................... 549/437
4,397,864  8/1983  Nakatani et al. ........... 549/445

FOREIGN PATENT DOCUMENTS 4920324  6/1972  Japan .
57-72928  5/1982  Japan .

OTHER PUBLICATIONS

CPI 79800V/46, dated 6/19/72.
Chemical Abstracts 86:189484a, (1977).

Primary Examiner—Ethel G. Love
Attorney, Agent, or Firm—Fisher, Christen & Sabol

[57] ABSTRACT

A 2-fluoroethoxy-substituted benzene derivative represented by the general formula

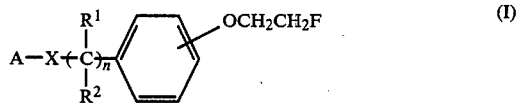

wherein X represents an oxygen or sulfur atom, $R^1$ and $R^2$ represent a hydrogen atom or a lower alkyl group, n represents 0 or 1, and A represents a group of the general formula

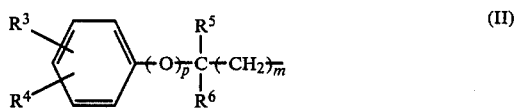

in which $R^3$ and $R^4$ represent a hydrogen atom, a halogen atom, a lower alkyl group, a lower alkoxy group, a lower alkylthio group, a lower haloalkyl group, a lower haloalkylthio group or a methylenedioxy group, $R^5$ and $R^6$ represent a hydrogen atom or a lower alkyl group, and p and m represent 0 or 1.

This compound is useful as an active ingredient of insecticidal and acaricidal agents, and can be produced by reacting a compound of the general formula

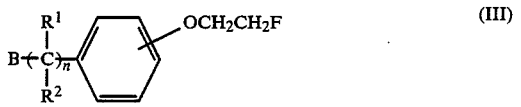

with a compound of the general formula

A—D  (IV)

wherein in general formulae (III) and (IV), A, $R^1$, $R^2$ and n are as defined above, and one of B and D represents a a halogen atom and the other represents a group of the general formula —X—M in which X is as defined above, and M represents a hydrogen atom or an alkali metal atom or an alkaline earth metal atom, provided that when n is 0, B is the group —X—M and D is a halogen atom.

11 Claims, No Drawings

2-FLUOROETHOXY-SUBSTITUTED BENZENE DERIVATIVES

This invention relates to novel 2-fluoroethoxy-substituted benzene derivatives, a process for production thereof, and insecticidal and acaricidal agents comprising these novel derivatives as active ingredients.

More specifically, this invention relates to 2-fluoroethoxy-substituted benzene derivatives represented by the general formula

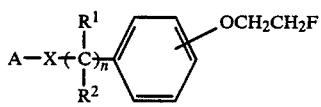
(I)

wherein X represents an oxygen or sulfur atom, $R^1$ and $R^2$ represent a hydrogen atom or a lower alkyl group, n represents 0 or 1, and A represents a group of the general formula

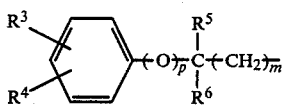
(II)

in which $R^3$ and $R^4$ represent a hydrogen atom, a halogen atom, a lower alkyl group, a lower alkoxy group, a lower alkylthio group, a lower haloalkyl group, a lower haloalkylthio group or a methylenedioxy group, $R^5$ and $R^6$ represent a hydrogen atom or a lower alkyl group, and p and m represent 0 or 1; a process for producing these derivatives; and insecticidal and acaricidal agents comprising these derivatives as active ingredients.

Various compounds including organochlorine compounds and organophosphorus compounds have been used for controlling acarids or mites. In recent years, acarids having reduced sensitivity to these chemicals have come into being, and it has become difficult to control them by the existing chemicals. New types of acaricides are therefore desired.

Investigations of the present inventors to provide acaricides which are economical and have high efficacy have now led to the discovery that the compounds represented by general formula (I) given above which are of a new and different type from conventional acaricides have excellent acaricidal activity.

The compounds of this invention are effective against plant-parasitic mites such as two-spotted spider mites *Tetranychus urticae* Koch), carmine spider mites (*Tetranychus cinnabarinus* Bolsdural) and citrus red mites (*Panonychus citri* McGregor). In particular, they show excellent acaricidal activity in the egg stage and the larval and young stages, and effectively contribute to the control of various sensitive and resistant acarids. The compounds of this invention also show effective insecticidal activity on lepidopterous pests such as common cutworm (*Spodoptera litura* Fabricius) and hemipterous pests such as small brown planthoppers (*Laodelphax striatellus* Fallén).

The compounds of this invention, i.e. 2-fluoroethoxy-substituted benzene derivatives represented by general formula (I), are novel.

3-(2-Fluoroethoxy)benzyl benzyl ether and 3-(2-fluoroethoxy)benzyl 2-(4-chlorophenyl)-2-methylpropyl ether, which are preferred examples of the compounds of this invention, have the structures represented by the formulae

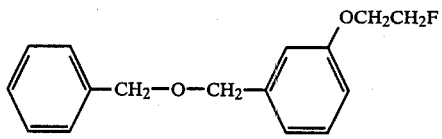

(a compound of general formula (I) in which X is an oxygen atom, $R^1$, $R^2$, $R^3$, $R^4$, $R^5$ and $R^6$ are all hydrogen atoms, p is 0, m is 0, n is 1, and the 2-fluoroethoxy group is substituted at the 3-position), and

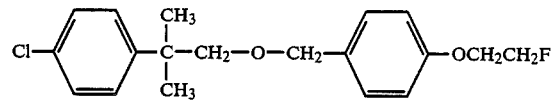

(a compound of general formula (I) in which X is an oxygen atom, $R^1$ and $R^2$ are hydrogen atoms, $R^3$ is a chlorine atom, $R^4$ is a hydrogen atom, $R^5$ and $R^6$ are methyl groups, p is 0, m and n are 1, and the 2-fluoroethoxy group is substituted at the 4-position).

3-(2-Fluoroethoxy)phenyl 3,4-dichlorobenzyl ether and 4-(2-fluoroethoxy)phenyl 4-chlorophenoxymethyl ether, which are other preferred examples of the compound of this invention, have the structures represented by the following formulae

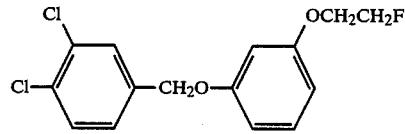

(a compound of general formula (I) in which X is an oxygen atom, $R^3$ and $R^4$ are chlorine atoms, $R^5$ and $R^6$ are hydrogen atoms, p, m, and n are zero, and the 2-fluoroethoxy group is substituted at the 3-position), and

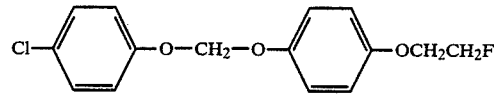

(a compound of general formula (I) in which X is an oxygen atom, $R^3$ is a chlorine atom, $R^4$, $R^5$ and $R^6$ are hydrogen atoms, p is 1, m and n are zero, and the 2-fluoroethoxy group is substituted at the 4-position).

In general formulae (I) and (II), the substituents $R^1$, $R^2$, $R^5$ and $R^6$ are hydrogen atoms or lower alkyl groups such as methyl, ethyl, n-propyl and iso-propyl groups. In these formulae, $R^3$ and $R^4$ are hydrogen atoms; halogen atoms such as fluorine, chlorine and bromine atoms; lower alkyl groups such as methyl, ethyl, isopropyl and tert-butyl groups; lower alkoxy groups such as methoxy, ethoxy, isopropoxy and tert-butoxy groups; lower alkylthio groups such as methylthio, ethylthio and isopropylthio groups; lower haloalkoxy groups such as difluoromethoxy groups, trifluoromethoxy groups, 2-fluoroethoxy groups and 2,2,2-trifluoroethoxy groups; lower haloalkylthio groups such as difluoromethylthio and 2-fluoroethylthio groups; and a 3,4-methylenedioxy group.

Examples of the compounds of this invention are tabulated in Table 1 for $R^1$, $R^2$, $R^3$, $R^4$, $R^5$, $R^6$, n, p, m and X and the substituted positions of $R^3$ and $R^4$ and the 2-fluoroethoxy group.

TABLE 1

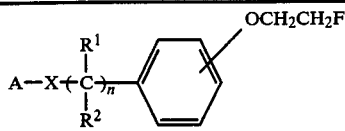 (I)

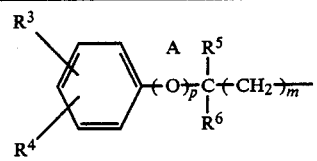 (II)

| Compound No. | $R^1$ | $R^2$ | X | n | A $R^3$ | $R^4$ | $R^5$ | $R^6$ | p | m | Position of $FCH_2CH_2O-$ | Physical constants |
|---|---|---|---|---|---|---|---|---|---|---|---|---|
| 1 | H | H | O | 1 | 4-Cl— | H | $CH_3$ | $CH_3$ | 0 | 1 | 3- | $\eta_D^{19.5} = 1.5453$ $C_{19}H_{22}ClFO_2$ |
| | | | | | | | | | | | | Calculated (%) / Found (%): C 67.75 / 67.69; H 6.58 / 6.72; Cl 10.53 / 10.38; F 5.64 / 5.49 |
| 2 | H | H | O | 1 | 4-$C_2H_5$O— | H | $CH_3$ | $CH_3$ | 0 | 1 | 3- | $\eta_D^{20.0} = 1.5354$ $C_{21}H_{27}FO_3$ |
| | | | | | | | | | | | | Calculated (%) / Found (%): C 72.80 / 72.91; H 7.86 / 7.81; F 5.48 / 5.43 |
| 3 | H | H | O | 1 | 4-Cl— | H | $CH_3$ | $CH_3$ | 0 | 1 | 4- | m.p. = 43–44° C. $C_{19}H_{22}ClFO_2$ |
| | | | | | | | | | | | | Calculated (%) / Found (%): C 67.75 / 67.92; H 6.58 / 6.43; Cl 10.53 / 10.32; F 5.64 / 5.69 |
| 4 | H | H | O | 1 | 4-$C_2H_5$O— | H | $CH_3$ | $CH_3$ | 0 | 1 | 4- | m.p. = 61–62° C. $C_{21}H_{27}FO_3$ |
| | | | | | | | | | | | | Calculated (%) / Found (%): C 72.80 / 72.60; H 7.86 / 7.79; F 5.48 / 5.57 |
| 5 | H | H | O | 1 | 4-Br— | H | $CH_3$ | $CH_3$ | 0 | 1 | 3- | $\eta_D^{20.0} = 1.5612$ $C_{19}H_{22}BrFO_2$ |
| | | | | | | | | | | | | Calculated (%) / Found (%): C 59.85 / 59.70; H 5.82 / 5.87; Br 20.96 / 20.44; F 4.98 / 4.99 |
| 6 | H | H | O | 1 | 4-$CH_2FCH_2$O— | H | $CH_3$ | $CH_3$ | 0 | 1 | 3- | $\eta_D^{20.8} = 1.5092$ $C_{21}H_{26}F_2O_3$ |
| | | | | | | | | | | | | Calculated (%) / Found (%): C 69.21 / 69.33; H 7.19 / 7.01; F 10.43 / 10.55 |
| 7 | H | H | S | 1 | 3-Cl— | 4-$C_2H_5$O— | $CH_3$ | $CH_3$ | 0 | 1 | 3- | $\eta_D^{20.0} = 1.5686$ $C_{21}H_{26}ClFO_2S$ |
| | | | | | | | | | | | | Calculated (%) / Found (%): C 63.54 / 63.72; H 6.60 / 6.54; Cl 8.93 / 8.89; F 4.79 / 4.61; S 8.08 / 8.20 |
| 8 | H | H | O | 1 | 3,4-$CH_2\langle{}^{O-}_{O-}$ | | $CH_3$ | $CH_3$ | 0 | 1 | 3- | $\eta_D^{20.0} = 1.5475$ $C_{20}H_{23}FO_4$ |
| | | | | | | | | | | | | Calculated (%) / Found (%): C 69.35 / 69.62 |

TABLE 1-continued $$A-X+C_{\overset{|}{R^2}}^{\overset{R^1}{|}}\!\!\!\!)_n\!\!-\!\!\bigg\langle\!\!\bigcirc\!\!\bigg\rangle\!\!-\!OCH_2CH_2F \quad (I)$$

$$\begin{array}{c}R^3\\ \\R^4\end{array}\!\!\bigg\langle\!\!\bigcirc\!\!\bigg\rangle\!\!-(O)_p\!\!\overset{\overset{R^5}{|}}{\underset{\overset{|}{R^6}}{C}}\!\!(CH_2)_m\!\!-\!A \quad (II)$$

| Compound No. | $R^1$ | $R^2$ | X | n | A $R^3$ | $R^4$ | $R^5$ | $R^6$ | p | m | Position of $FCH_2CH_2O-$ | Physical constants |
|---|---|---|---|---|---|---|---|---|---|---|---|---|
| | | | | | | | | | | | | H 6.69 6.53 |
| | | | | | | | | | | | | F 5.49 5.37 |
| 9 | H | H | O | 1 | 4-CH$_3$S— | H | CH$_3$ | CH$_3$ | 0 | 1 | 3- | $\eta_D^{20.0}$ = 1.5676 |
| | | | | | | | | | | | | C$_{20}$H$_{25}$FO$_2$S |
| | | | | | | | | | | | |     Calculated (%)   Found (%) |
| | | | | | | | | | | | | C    68.93    68.99 |
| | | | | | | | | | | | | H    7.23    7.32 |
| | | | | | | | | | | | | F    5.45    5.41 |
| | | | | | | | | | | | | S    9.20    9.22 |
| 10 | H | H | O | 1 | 4-CH$_3$-C(CH$_3$)(CH$_3$)- | H | CH$_3$ | CH$_3$ | 0 | 1 | 3- | $\eta_D^{20.6}$ = 1.5292 |
| | | | | | | | | | | | | C$_{23}$H$_{31}$FO$_3$ |
| | | | | | | | | | | | |     Calculated (%)   Found (%) |
| | | | | | | | | | | | | C    73.76    73.94 |
| | | | | | | | | | | | | H    8.34    8.35 |
| | | | | | | | | | | | | F    5.07    4.98 |
| 11 | H | H | O | 1 | 4-CHF$_2$O— | H | CH$_3$ | CH$_3$ | 0 | 1 | 3- | $\eta_D^{20.0}$ = 1.5141 |
| | | | | | | | | | | | | C$_{20}$H$_{23}$F$_2$O$_3$ |
| | | | | | | | | | | | |     Calculated (%)   Found (%) |
| | | | | | | | | | | | | C    65.20    65.31 |
| | | | | | | | | | | | | H    6.29    6.25 |
| | | | | | | | | | | | | F    15.47    15.32 |
| 12 | H | H | O | 1 | 4-CHF$_2$CF$_2$O— | H | CH$_3$ | CH$_3$ | 0 | 1 | 3- | $\eta_D^{20.0}$ = 1.4928 |
| | | | | | | | | | | | | C$_{21}$H$_{23}$F$_5$O$_3$ |
| | | | | | | | | | | | |     Calculated (%)   Found (%) |
| | | | | | | | | | | | | C    60.28    60.51 |
| | | | | | | | | | | | | H    5.54    5.61 |
| | | | | | | | | | | | | F    22.71    22.53 |
| 13 | H | H | O | 1 | 4-CH$_3$S— | H | CH$_3$ | CH$_3$ | 0 | 1 | 4- | $\eta_D^{20.4}$ = 1.5678 |
| | | | | | | | | | | | | C$_{20}$H$_{25}$FO$_2$S |
| | | | | | | | | | | | |     Calculated (%)   Found (%) |
| | | | | | | | | | | | | C    68.93    68.89 |
| | | | | | | | | | | | | H    7.23    7.25 |
| | | | | | | | | | | | | F    5.45    5.41 |
| | | | | | | | | | | | | S    9.20    9.19 |
| 14 | H | H | O | 1 | 3,4-CH$_2$(-O-)(-O-) | | CH$_3$ | CH$_3$ | 0 | 1 | 4- | $\eta_D^{20.9}$ = 1.5483 |
| | | | | | | | | | | | | C$_{20}$H$_{23}$FO$_4$ |
| | | | | | | | | | | | |     Calculated (%)   Found (%) |
| | | | | | | | | | | | | C    67.77    67.91 |
| | | | | | | | | | | | | H    8.82    8.64 |
| | | | | | | | | | | | | F    5.36    5.42 |
| 15 | H | H | O | 1 | 4-CH$_3$-C(CH$_3$)(CH$_3$)- | H | CH$_3$ | CH$_3$ | 0 | 1 | 4- | m.p. = 46.2–47.6° C. |
| | | | | | | | | | | | | C$_{23}$H$_{31}$FO$_2$ |
| | | | | | | | | | | | |     Calculated (%)   Found (%) |
| | | | | | | | | | | | | C    77.06    77.30 |
| | | | | | | | | | | | | H    8.72    8.51 |
| | | | | | | | | | | | | F    5.30    5.27 |

TABLE 1-continued $$A-X{-}{\underset{R^2}{\overset{R^1}{C}}}{-}_n\text{−}\!\!\bigcirc\!\!\text{−}OCH_2CH_2F \quad (I)$$

$$\underset{R^4}{\overset{R^3}{\phantom{A}}}\!\!\bigcirc\!\!{-}(O)_p{-}{\underset{R^6}{\overset{R^5}{C}}}{-}(CH_2)_m{-}A \quad (II)$$

| Compound No. | R¹ | R² | X | n | R³ | R⁴ | R⁵ | R⁶ | p | m | Position of $FCH_2CH_2O{-}$ | Physical constants |
|---|---|---|---|---|---|---|---|---|---|---|---|---|
| 16 | H | H | O | 1 | 4-$(CH_3)_2CH{-}$ | H | $CH_3$ | $CH_3$ | 0 | 1 | 4- | $\eta_D^{20.2} = 1.5310$ $C_{22}H_{29}FO_2$ Calculated (%): C 76.71, H 8.49, F 5.52 Found (%): C 76.74, H 8.51, F 5.49 |
| 17 | H | H | O | 1 | 4-Br— | H | $CH_3$ | $CH_3$ | 0 | 1 | 4- | m.p. = 56–57° C. $C_{19}H_{22}BrFO_2$ Calculated (%): C 59.85, H 5.82, Br 20.96, F 4.98 Found (%): C 59.92, H 5.93, Br 20.70, F 4.95 |
| 18 | H | H | O | 1 | 4-$CH_2FCH_2O{-}$ | H | $CH_3$ | $CH_3$ | 0 | 1 | 4- | m.p. = 78.0–79.8° C. $C_{21}H_{26}F_2O_3$ Calculated (%): C 69.21, H 7.19, F 10.43 Found (%): C 69.40, H 7.21, F 10.52 |
| 19 | H | H | O | 1 | 4-$(CH_3)_2CHO{-}$ | H | $CH_3$ | $CH_3$ | 0 | 1 | 4- | $\eta_D^{19.7} = 1.5339$ $C_{22}H_{29}FO_3$ Calculated (%): C 73.30, H 8.11, F 5.27 Found (%): C 73.51, H 8.01, F 5.14 |
| 20 | H | H | O | 1 | 4-$C_2H_5{-}$ | H | $CH_3$ | $CH_3$ | 0 | 1 | 4- | $\eta_D^{20.4} = 1.5364$ $C_{21}H_{27}FO_2$ Calculated (%): C 76.33, H 8.24, F 5.75 Found (%): C 76.51, H 8.31, F 5.58 |
| 21 | H | H | O | 1 | 4-$CF_2HO{-}$ | H | $CH_3$ | $CH_3$ | 0 | 1 | 4- | $\eta_D^{19.9} = 1.5172$ $C_{20}H_{23}F_3O_3$ Calculated (%): C 65.20, H 6.29, F 15.47 Found (%): C 65.41, H 6.13, F 15.42 |
| 22 | H | H | S | 1 | 4-$(CH_3)_3C{-}$ | H | $CH_3$ | $CH_3$ | 0 | 1 | 4- | $\eta_D^{20.6} = 1.5529$ $C_{23}H_{31}FOS$ Calculated (%): C 73.75, H 8.34, F 5.07, S 8.56 Found (%): C 77.87, H 8.21, F 5.11, S 8.32 |
| 23 | H | H | S | 1 | 3-Cl— | 4-$C_2H_5O{-}$ | $CH_3$ | $CH_3$ | 0 | 1 | 4- | $\eta_D^{19.4} = 1.5639$ $C_{21}H_{26}ClFO_2S$ Calculated (%): C 63.54, H 6.60, Cl 8.93 Found (%): C 63.72, H 6.51, Cl 8.79 |

TABLE 1-continued $$A-X{\left(C\right)}_{n}^{R^1}_{R^2}-\!\!\bigcirc\!\!-OCH_2CH_2F \quad (I)$$

$$\begin{matrix}R^3\\R^4\end{matrix}\!\!\bigcirc\!\!-(O)_p\overset{R^5}{\underset{R^6}{C}}(CH_2)_m-A \quad (II)$$

| Compound No. | R¹ | R² | X | n | A R³ | R⁴ | R⁵ | R⁶ | p | m | Position of $FCH_2CH_2O-$ | Physical constants | | |
|---|---|---|---|---|---|---|---|---|---|---|---|---|---|---|
| 24 | H | H | O | 1 | 4-CHF₂CF₂O— | H | CH₃ | CH₃ | 0 | 1 | 4- | F 4.79 / 4.92<br>S 8.08 / 8.21<br>$\eta_D^{20.1} = 1.4958$<br>C₂₁H₂₃F₅O₃ | | |
|  |  |  |  |  |  |  |  |  |  |  |  |  | Calculated (%) | Found (%) |
|  |  |  |  |  |  |  |  |  |  |  |  | C | 60.28 | 60.51 |
|  |  |  |  |  |  |  |  |  |  |  |  | H | 5.54 | 5.49 |
| 25 | H | H | O | 1 | 4-Cl— | H | CH₃ | CH₃ | 0 | 1 | 2- | F 22.71 / 22.50<br>m.p. = 58–59° C.<br>C₁₉H₂₂ClFO₂ | | |
|  |  |  |  |  |  |  |  |  |  |  |  |  | Calculated (%) | Found (%) |
|  |  |  |  |  |  |  |  |  |  |  |  | C | 67.75 | 68.01 |
|  |  |  |  |  |  |  |  |  |  |  |  | H | 6.58 | 6.37 |
|  |  |  |  |  |  |  |  |  |  |  |  | Cl | 10.53 | 10.41 |
| 26 | H | H | O | 1 | 4-Cl— | H | C₂H₅ | H | 0 | 1 | 3- | F 5.64 / 5.71<br>$\eta_D^{20.3} = 1.5433$<br>C₁₉H₂₂ClFO₂ | | |
|  |  |  |  |  |  |  |  |  |  |  |  |  | Calculated (%) | Found (%) |
|  |  |  |  |  |  |  |  |  |  |  |  | C | 67.75 | 67.92 |
|  |  |  |  |  |  |  |  |  |  |  |  | H | 6.58 | 6.49 |
|  |  |  |  |  |  |  |  |  |  |  |  | Cl | 10.53 | 10.27 |
| 27 | H | H | O | 1 | 3-Cl— | 4-Cl— | CH₃ | CH₃ | 0 | 1 | 2- | F 5.64 / 5.73<br>$\eta_D^{20.1} = 1.5542$<br>C₁₉H₂₁Cl₂FO₂ | | |
|  |  |  |  |  |  |  |  |  |  |  |  |  | Calculated (%) | Found (%) |
|  |  |  |  |  |  |  |  |  |  |  |  | C | 61.46 | 61.57 |
|  |  |  |  |  |  |  |  |  |  |  |  | H | 5.70 | 5.69 |
|  |  |  |  |  |  |  |  |  |  |  |  | Cl | 19.10 | 19.32 |
| 28 | H | H | O | 1 | 3-Cl— | 4-Cl— | CH₃ | CH₃ | 0 | 1 | 3- | F 5.12 / 5.01<br>$\eta_D^{19.6} = 1.5561$<br>C₁₉H₂₁Cl₂FO₂ | | |
|  |  |  |  |  |  |  |  |  |  |  |  |  | Calculated (%) | Found (%) |
|  |  |  |  |  |  |  |  |  |  |  |  | C | 61.46 | 61.72 |
|  |  |  |  |  |  |  |  |  |  |  |  | H | 5.70 | 5.89 |
|  |  |  |  |  |  |  |  |  |  |  |  | Cl | 19.10 | 19.21 |
| 29 | H | H | O | 1 | 3-Cl— | 4-Cl— | CH₃ | CH₃ | 0 | 1 | 4- | F 5.12 / 5.21<br>$\eta_D^{20.0} = 1.5558$<br>C₁₉H₂₁Cl₂FO₂ | | |
|  |  |  |  |  |  |  |  |  |  |  |  |  | Calculated (%) | Found (%) |
|  |  |  |  |  |  |  |  |  |  |  |  | C | 61.46 | 61.71 |
|  |  |  |  |  |  |  |  |  |  |  |  | H | 5.70 | 5.82 |
|  |  |  |  |  |  |  |  |  |  |  |  | F | 19.10 | 18.92 |
| 30 | H | H | O | 1 | 2-Cl— | 4-Cl— | CH₃ | CH₃ | 0 | 1 | 2- | Cl 5.12 / 4.99<br>$\eta_D^{20.3} = 1.5525$<br>C₁₉H₂₁Cl₂FO₂ | | |
|  |  |  |  |  |  |  |  |  |  |  |  |  | Calculated (%) | Found (%) |
|  |  |  |  |  |  |  |  |  |  |  |  | C | 61.46 | 61.52 |
|  |  |  |  |  |  |  |  |  |  |  |  | H | 5.70 | 5.63 |
|  |  |  |  |  |  |  |  |  |  |  |  | F | 19.10 | 19.20 |
| 31 | H | H | O | 1 | 2-Cl— | 4-Cl— | CH₃ | CH₃ | 0 | 1 | 3- | Cl 5.12 / 5.13<br>$\eta_D^{19.1} = 1.5568$<br>C₁₉H₂₁Cl₂FO₂ | | |
|  |  |  |  |  |  |  |  |  |  |  |  |  | Calculated (%) | Found (%) |
|  |  |  |  |  |  |  |  |  |  |  |  | C | 61.46 | 61.63 |
|  |  |  |  |  |  |  |  |  |  |  |  | H | 5.70 | 5.80 |
|  |  |  |  |  |  |  |  |  |  |  |  | Cl | 19.10 | 18.93 |
| 32 | H | H | O | 1 | 2-Cl— | 4-Cl— | CH₃ | CH₃ | 0 | 1 | 4- | F 5.12 / 5.23<br>$\eta_D^{19.2} = 1.5556$<br>C₁₉H₂₁Cl₂FO₂ | | |
|  |  |  |  |  |  |  |  |  |  |  |  |  | Cal | Found |

TABLE 1-continued $$A-X+\underset{R^2}{\overset{R^1}{C}}\underset{n}{}\text{—Ar—OCH}_2\text{CH}_2\text{F} \quad (I)$$

$$\text{Ar}(R^3)(R^4)\text{—}(\text{O})_p\text{—}\underset{R^6}{\overset{R^5}{C}}\text{—}(CH_2)_m\text{—A} \quad (II)$$

| Compound No. | R¹ | R² | X | n | R³ | R⁴ | R⁵ | R⁶ | p | m | Position of FCH₂CH₂O— | Physical constants | | |
|---|---|---|---|---|---|---|---|---|---|---|---|---|---|---|
| | | | | | | | | | | | | | Calculated (%) | Found (%) |
| | | | | | | | | | | | | C | 61.46 | 61.39 |
| | | | | | | | | | | | | H | 5.70 | 5.73 |
| | | | | | | | | | | | | Cl | 19.10 | 19.05 |
| | | | | | | | | | | | | F | 5.12 | 5.18 |
| 33 | H | H | O | 1 | H | H | CH₃ | CH₃ | 0 | 1 | 2- | $\eta_D^{18.5} = 1.5389$ C₁₉H₂₃FO₂ | | |
| | | | | | | | | | | | | | Calculated (%) | Found (%) |
| | | | | | | | | | | | | C | 75.47 | 75.52 |
| | | | | | | | | | | | | H | 7.67 | 7.81 |
| | | | | | | | | | | | | F | 6.28 | 6.09 |
| 34 | H | H | O | 1 | H | H | CH₃ | CH₃ | 0 | 1 | 3- | $\eta_D^{19.6} = 1.5399$ C₁₉H₂₃FO₂ | | |
| | | | | | | | | | | | | | Calculated (%) | Found (%) |
| | | | | | | | | | | | | C | 75.47 | 75.62 |
| | | | | | | | | | | | | H | 7.67 | 7.58 |
| | | | | | | | | | | | | F | 6.28 | 6.29 |
| 35 | H | H | O | 1 | H | H | CH₃ | CH₃ | 0 | 1 | 4- | $\eta_D^{19.8} = 1.5392$ C₁₉H₂₃FO₂ | | |
| | | | | | | | | | | | | | Calculated (%) | Found (%) |
| | | | | | | | | | | | | C | 75.47 | 75.73 |
| | | | | | | | | | | | | H | 7.67 | 7.71 |
| | | | | | | | | | | | | F | 6.28 | 6.14 |
| 36 | H | H | O | 1 | 4-CH₃— | H | CH₃ | CH₃ | 0 | 1 | 2- | $\eta_D^{20.0} = 1.5364$ C₂₀H₂₅FO₂ | | |
| | | | | | | | | | | | | | Calculated (%) | Found (%) |
| | | | | | | | | | | | | C | 75.92 | 76.03 |
| | | | | | | | | | | | | H | 7.96 | 8.02 |
| | | | | | | | | | | | | F | 6.01 | 5.84 |
| 37 | H | H | O | 1 | 4-CH₃— | H | CH₃ | CH₃ | 0 | 1 | 3- | $\eta_D^{20.2} = 1.5388$ C₂₀H₂₅FO₂ | | |
| | | | | | | | | | | | | | Calculated (%) | Found (%) |
| | | | | | | | | | | | | C | 75.92 | 75.89 |
| | | | | | | | | | | | | H | 7.96 | 7.95 |
| | | | | | | | | | | | | F | 6.01 | 6.13 |
| 38 | H | H | O | 1 | 4-CH₃— | H | CH₃ | CH₃ | 0 | 1 | 4- | $\eta_D^{20.4} = 1.5374$ C₂₀H₂₅FO₂ | | |
| | | | | | | | | | | | | | Calculated (%) | Found (%) |
| | | | | | | | | | | | | C | 75.92 | 76.12 |
| | | | | | | | | | | | | H | 7.96 | 8.03 |
| | | | | | | | | | | | | F | 6.01 | 5.82 |
| 39 | H | H | O | 1 | 4-C₂H₅— | H | CH₃ | CH₃ | 0 | 1 | 2- | $\eta_D^{18.8} = 1.5338$ C₂₁H₂₇FO₂ | | |
| | | | | | | | | | | | | | Calculated (%) | Found (%) |
| | | | | | | | | | | | | C | 76.33 | 76.51 |
| | | | | | | | | | | | | H | 8.24 | 8.16 |
| | | | | | | | | | | | | F | 5.75 | 5.81 |
| 40 | H | H | O | 1 | H | H | H | H | 0 | 1 | 4- | $\eta_D^{20.1} = 1.5470$ C₁₇H₁₉FO₂ | | |
| | | | | | | | | | | | | | Calculated (%) | Found (%) |
| | | | | | | | | | | | | C | 74.43 | 74.52 |
| | | | | | | | | | | | | H | 6.98 | 7.07 |
| | | | | | | | | | | | | F | 6.93 | 6.85 |
| 41 | H | H | O | 1 | 4-C₂H₅— | H | CH₃ | CH₃ | 0 | 1 | 3- | $\eta_D^{19.1} = 1.5353$ C₂₁H₂₇FO₂ | | |
| | | | | | | | | | | | | | Calculated (%) | Found (%) |
| | | | | | | | | | | | | C | 76.33 | 76.58 |
| | | | | | | | | | | | | H | 8.24 | 8.37 |
| | | | | | | | | | | | | F | 5.75 | 5.60 |

TABLE 1-continued $$A-X\overset{R^1}{\underset{R^2}{+C+_n}}\text{—Ar—OCH}_2\text{CH}_2\text{F} \quad (I)$$

$$\text{Ar}(R^3)(R^4)\text{—}(O)_p\overset{R^5}{\underset{R^6}{+C+}}(\text{CH}_2)_m\text{—A} \quad (II)$$

| Compound No. | R¹ | R² | X | n | A R³ | R⁴ | R⁵ | R⁶ | p | m | Position of FCH₂CH₂O— | Physical constants |
|---|---|---|---|---|---|---|---|---|---|---|---|---|
| 42 | H | H | O | 1 | 4-CH₃O— | H | C₂H₅ | H | 0 | 1 | 3- | $\eta_D^{19.6}$ = 1.5387; C₂₀H₂₅FO₃; Calculated (%): C 72.26, H 7.58, F 5.72; Found (%): C 72.41, H 7.67, F 5.71 |
| 43 | H | H | O | 1 | 3-Cl— | 4-Cl— | (CH₃)₂CH— | H | 0 | 1 | 2- | $\eta_D^{20.7}$ = 1.5503; C₂₀H₂₃Cl₂FO₂; Calculated (%): C 62.34, H 6.02, Cl 18.40, F 4.93; Found (%): C 62.51, H 6.13, Cl 18.10, F 4.88 |
| 44 | H | H | O | 1 | 4-CH₃O— | H | C₂H₅ | H | 0 | 1 | 4- | $\eta_D^{19.6}$ = 1.5380; C₂₀H₂₅FO₃; Calculated (%): C 72.26, H 7.58, F 5.72; Found (%): C 72.16, H 7.63, F 5.76 |
| 45 | H | H | O | 1 | 3-Cl— | 4-Cl— | (CH₃)₂CH— | H | 0 | 1 | 3- | $\eta_D^{21.1}$ = 1.5498; C₂₀H₂₃ClFO₂; Calculated (%): C 62.34, H 6.02, F 18.40, Cl 4.93; Found (%): C 62.51, H 6.13, F 18.10, Cl 4.98 |
| 46 | H | H | O | 1 | 3-Cl— | 4-Cl— | CH₃ | H | 0 | 1 | 3- | $\eta_D^{21.0}$ = 1.5624; C₁₈H₁₉Cl₂FO₂; Calculated (%): C 60.51, H 5.32, Cl 19.85, F 5.32; Found (%): C 60.58, H 5.37, Cl 19.77, F 5.24 |
| 47 | H | H | O | 1 | 3-Cl— | 4-Cl— | (CH₃)₂CH— | H | 0 | 1 | 3- | $\eta_D^{20.3}$ = 1.5499; C₂₀H₂₃Cl₂FO₂; Calculated (%): C 62.34, H 6.02, Cl 18.40, F 4.93; Found (%): C 62.51, H 6.09, Cl 18.20, F 5.01 |
| 48 | — | — | O | 0 | H | H | H | H | 0 | 0 | 4- | m.p. = 76.6–77.3° C.; C₁₅H₁₅FO₂; Calculated (%): C 73.15, H 6.14, F 7.72; Found (%): C 73.05, H 6.17, F 7.98 |
| 49 | — | — | O | 0 | 4-Cl— | H | H | H | 0 | 0 | 4- | m.p. = 63.5–64.7° C.; C₁₅H₁₄ClFO₂ |

4,552,894

TABLE 1-continued $$\text{A—X} \overset{R^1}{\underset{R^2}{\overset{|}{\text{—C—}}}}_n \text{—} \bigcirc \text{—OCH}_2\text{CH}_2\text{F} \quad \text{(I)}$$

$$\underset{R^4}{\overset{R^3}{\bigcirc}} \text{—}(\text{O})_p\overset{R^5}{\underset{R^6}{\overset{|}{\text{—C—}}}}(\text{CH}_2)_m\text{—A} \quad \text{(II)}$$

| Compound No. | R¹ | R² | X | n | R³ | R⁴ | R⁵ | R⁶ | p | m | Position of FCH₂CH₂O— | Physical constants | | |
|---|---|---|---|---|---|---|---|---|---|---|---|---|---|---|
| | | | | | | | | | | | | | Calculated (%) | Found (%) |
| | | | | | | | | | | | | C | 64.17 | 64.08 |
| | | | | | | | | | | | | H | 5.03 | 5.02 |
| | | | | | | | | | | | | Cl | 12.63 | 12.66 |
| | | | | | | | | | | | | F | 6.77 | 6.74 |
| 50 | — | — | O | 0 | 4-CH₃— | H | H | H | 0 | 0 | 4- | m.p. = 73–74° C. C₁₆H₁₇FO₂ | | |
| | | | | | | | | | | | | | Calculated (%) | Found (%) |
| | | | | | | | | | | | | C | 73.82 | 73.94 |
| | | | | | | | | | | | | H | 6.58 | 6.60 |
| | | | | | | | | | | | | F | 7.30 | 7.41 |
| 51 | — | — | O | 0 | 4-(CH₃)₂CH— | H | H | H | 0 | 0 | 4- | m.p. = 60–61° C. C₁₈H₂₁FO₂ | | |
| | | | | | | | | | | | | | Calculated (%) | Found (%) |
| | | | | | | | | | | | | C | 74.97 | 74.97 |
| | | | | | | | | | | | | H | 7.34 | 7.51 |
| | | | | | | | | | | | | F | 6.58 | 6.62 |
| 52 | — | — | O | 0 | 4-Br— | H | H | H | 0 | 0 | 4- | m.p. = 108–109° C. C₁₅H₁₄BrFO₂ | | |
| | | | | | | | | | | | | | Calculated (%) | Found (%) |
| | | | | | | | | | | | | C | 55.40 | 55.43 |
| | | | | | | | | | | | | H | 4.34 | 4.52 |
| | | | | | | | | | | | | Br | 24.58 | 24.65 |
| | | | | | | | | | | | | F | 5.84 | 5.91 |
| 53 | — | — | O | 0 | 4-C₂H₅— | H | CH₃ | CH₃ | 0 | 1 | 4- | $\eta_D^{19.0}$ = 1.5405 C₂₀H₂₅FO₂ | | |
| | | | | | | | | | | | | | Calculated (%) | Found (%) |
| | | | | | | | | | | | | C | 75.92 | 76.03 |
| | | | | | | | | | | | | H | 7.96 | 7.86 |
| | | | | | | | | | | | | F | 6.01 | 6.30 |
| 54 | — | — | O | 0 | H | H | H | H | 0 | 1 | 4- | $\eta_D^{19.6}$ = 1.5550 C₁₆H₁₇FO₂ | | |
| | | | | | | | | | | | | | Calculated (%) | Found (%) |
| | | | | | | | | | | | | C | 73.82 | 73.81 |
| | | | | | | | | | | | | H | 6.58 | 6.59 |
| | | | | | | | | | | | | F | 7.30 | 7.28 |
| 55 | — | — | O | 0 | 3-Cl— | 4-C₂H₅O— | CH₃ | CH₃ | 0 | 1 | 4- | m.p. 63.5–64.7° C. C₂₀H₂₄ClFO₂ | | |
| | | | | | | | | | | | | | Calculated (%) | Found (%) |
| | | | | | | | | | | | | C | 65.48 | 65.45 |
| | | | | | | | | | | | | H | 6.59 | 6.61 |
| | | | | | | | | | | | | Cl | 9.67 | 9.62 |
| | | | | | | | | | | | | F | 5.18 | 5.11 |
| 56 | — | — | O | 0 | 4-CH₃— | H | H | H | 0 | 1 | 4- | m.p. = 70–71° C. C₁₇H₁₉FO₂ | | |
| | | | | | | | | | | | | | Calculated (%) | Found (%) |
| | | | | | | | | | | | | C | 74.43 | 74.40 |
| | | | | | | | | | | | | H | 6.98 | 6.64 |
| | | | | | | | | | | | | F | 6.93 | 6.58 |
| 57 | — | — | O | 0 | 2-Cl— | 6-Cl— | H | H | 0 | 0 | 4- | m.p. = 96–97° C. C₁₅H₁₃Cl₂FO₂ | | |
| | | | | | | | | | | | | | Calculated (%) | Found (%) |
| | | | | | | | | | | | | C | 57.16 | 57.31 |
| | | | | | | | | | | | | H | 4.16 | 4.24 |

TABLE 1-continued $$A-X(C)_n \text{-Ar-OCH}_2\text{CH}_2\text{F} \quad (I)$$
with $R^1$, $R^2$ on C $$\text{Ar}(R^3)(R^4)\text{-O}_p\text{-C}(R^5)(R^6)\text{-(CH}_2)_m\text{-A} \quad (II)$$

| Compound No. | $R^1$ | $R^2$ | X | n | $R^3$ | $R^4$ | A $R^5$ | $R^6$ | p | m | Position of FCH$_2$CH$_2$O— | Physical constants |
|---|---|---|---|---|---|---|---|---|---|---|---|---|
| 58 | — | — | O | 0 | 3-CH$_3$— | 4-CH$_3$— | H | H | 0 | 0 | 4- | Cl 22.50 22.63<br>F 6.03 6.21<br>m.p. = 45–46° C.<br>C$_{17}$H$_{19}$FO$_2$<br>Calculated (%) / Found (%)<br>C 74.43 74.51<br>H 6.98 7.11<br>F 6.93 7.05 |
| 59 | — | — | O | 0 | 4-C$_2$H$_5$— | H | H | H | 0 | 0 | 4- | C$_{17}$H$_{19}$FO$_2$<br>Calculated (%) / Found (%)<br>C 74.43 74.55<br>H 6.98 6.82<br>F 6.93 6.84<br>$\delta^{CCl_4}_{TMS}$ (ppm): 1.23(t,3H), 2.59 (q,2H), 3.76–3.86(m,1H), 4.03–4.12(m,1H), 4.24–4.32 (m,1H), 4.72–4.81(m,1H), 4.84(s,2H), 6.69–7.34(m,2H) |
| 60 | — | — | O | 0 | 3-Cl— | 4-Cl— | H | H | 0 | 0 | 4- | m.p. = 62–63° C.<br>C$_{15}$H$_{13}$Cl$_2$FO$_2$<br>Calculated (%) / Found (%)<br>C 57.16 57.11<br>H 4.16 4.26<br>Cl 22.50 22.68<br>F 6.03 6.01 |
| 61 | — | — | O | 0 | 2-Cl— | 4-Cl— | H | H | 0 | 0 | 4- | m.p. = 83–83.7° C.<br>C$_{15}$H$_{13}$Cl$_2$FO$_2$<br>Calculated (%) / Found (%)<br>C 57.16 57.22<br>H 4.16 4.34<br>Cl 22.50 22.65<br>F 6.03 6.23 |
| 62 | — | — | O | 0 | 3,4-CH(—O—)(—O—) | | H | H | 0 | 0 | 4- | m.p. = 81.5–82.2° C.<br>C$_{16}$H$_{15}$FO$_4$<br>Calculated (%) / Found (%)<br>C 66.20 66.24<br>H 5.21 5.33<br>F 6.55 6.75 |
| 63 | — | — | O | 0 | 4-Cl— | H | H | H | 0 | 0 | 3- | $\eta_D^{20.8}$ = 1.5700<br>C$_{15}$H$_{14}$ClFO$_2$<br>Calculated (%) / Found (%)<br>C 64.17 64.31<br>H 5.03 5.00<br>Cl 12.63 12.65<br>F 6.77 6.83 |
| 64 | — | — | O | 0 | 4-CH(CH$_3$)$_2$ | H | H | H | 0 | 0 | 3- | $\eta_D^{20.9}$ = 1.5476<br>C$_{18}$H$_{21}$FO$_2$<br>Calculated (%) / Found (%)<br>C 74.97 75.06<br>H 7.34 7.55<br>F 6.59 6.53 |
| 65 | — | — | O | 0 | 3-Cl— | 4-Cl | H | H | 0 | 0 | 3- | $\eta_D^{21.0}$ = 1.5801<br>C$_{15}$H$_{13}$Cl$_2$FO$_2$<br>Calculated (%) / Found (%) |

TABLE 1-continued

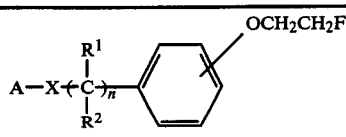 (I)   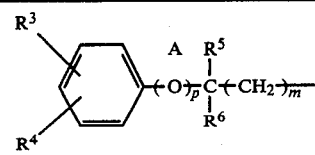 (II)

| Compound No. | R¹ | R² | X | n | R³ | A R⁴ | R⁵ | R⁶ | p | m | Position of FCH₂CH₂O— | Physical constants | | |
|---|---|---|---|---|---|---|---|---|---|---|---|---|---|---|
| | | | | | | | | | | | | C | 57.16 | 57.03 |
| | | | | | | | | | | | | H | 4.16 | 4.12 |
| | | | | | | | | | | | | Cl | 22.50 | 22.54 |
| | | | | | | | | | | | | F | 6.03 | 6.15 |
| 66 | — | — | O | 0 | H | H | H | H | 0 | 0 | 3- | $\eta_D^{21.1}$ = 1.5620 $C_{15}H_{15}FO_2$ | | |
| | | | | | | | | | | | | | Calculated (%) | Found (%) |
| | | | | | | | | | | | | C | 73.15 | 73.17 |
| | | | | | | | | | | | | H | 6.14 | 6.03 |
| | | | | | | | | | | | | F | 7.72 | 7.63 |
| 67 | — | — | O | 0 | 3,4-CH₂⟨O—/O—⟩ | | H | H | 0 | 0 | 3- | $\eta_D^{21.2}$ = 1.5755 $C_{16}H_{15}FO_4$ | | |
| | | | | | | | | | | | | | Calculated (%) | Found (%) |
| | | | | | | | | | | | | C | 66.20 | 66.31 |
| | | | | | | | | | | | | H | 5.21 | 5.03 |
| | | | | | | | | | | | | F | 6.55 | 6.63 |
| 68 | — | — | O | 0 | 4-CH₃— | H | H | H | 0 | 0 | 3- | $\eta_D^{21.2}$ = 1.5581 $C_{16}H_{17}FO_2$ | | |
| | | | | | | | | | | | | | Calculated (%) | Found (%) |
| | | | | | | | | | | | | C | 73.82 | 73.72 |
| | | | | | | | | | | | | H | 6.58 | 6.55 |
| | | | | | | | | | | | | F | 7.30 | 7.58 |
| 69 | — | — | O | 0 | 4-C₂H₅— | H | H | H | 0 | 0 | 3- | $\eta_D^{20.6}$ = 1.5548 $C_{17}H_{19}FO_2$ | | |
| | | | | | | | | | | | | | Calculated (%) | Found (%) |
| | | | | | | | | | | | | C | 74.43 | 74.56 |
| | | | | | | | | | | | | H | 6.98 | 7.03 |
| | | | | | | | | | | | | F | 6.93 | 6.80 |
| 70 | — | — | O | 0 | 3-CH₃— | 4-CH₃— | H | H | 0 | 0 | 3- | $\eta_D^{20.2}$ = 1.5619 $C_{17}H_{19}FO_2$ | | |
| | | | | | | | | | | | | | Calculated (%) | Found (%) |
| | | | | | | | | | | | | C | 74.43 | 74.58 |
| | | | | | | | | | | | | H | 6.98 | 7.03 |
| | | | | | | | | | | | | F | 6.93 | 6.87 |
| 71 | — | — | O | 0 | 3-Cl— | 4-C₂H₅O— | H | H | 0 | 0 | 3- | $\eta_D^{20.6}$ = 1.5692 $C_{17}H_{18}ClFO_2$ | | |
| | | | | | | | | | | | | | Calculated (%) | Found (%) |
| | | | | | | | | | | | | C | 62.87 | 63.05 |
| | | | | | | | | | | | | H | 5.59 | 5.68 |
| | | | | | | | | | | | | Cl | 10.92 | 10.71 |
| | | | | | | | | | | | | F | 5.85 | 5.91 |
| 72 | — | — | O | 0 | 3-Cl— | 4-C₂H₅O— | H | H | 0 | 0 | 4- | $C_{17}H_{18}ClFO_3$ | | |
| | | | | | | | | | | | | | Calculated (%) | Found (%) |
| | | | | | | | | | | | | C | 62.87 | 62.99 |
| | | | | | | | | | | | | H | 5.59 | 5.67 |
| | | | | | | | | | | | | Cl | 10.92 | 10.80 |
| | | | | | | | | | | | | F | 5.85 | 5.77 |
| | | | | | | | | | | | | $\delta_{THS}^{CCl_4}$(ppm): 1.44(t,3H), 3.98(q,2H),4.79(s,2H), 3.82–3.92(m,1H),4.07–4.19 (m,1H),4.28–4.37(m,1H), 4.72–4.83(m,1H),6.24–7.28 (m,7H) | | |
| 73 | — | — | O | 0 | 4-CH₂FCH₂O— | H | H | H | 0 | 0 | 4- | m.p. = 121.8–123.0° C. $C_{17}H_{18}F_2O_3$ | | |
| | | | | | | | | | | | | | Calculated (%) | Found (%) |
| | | | | | | | | | | | | C | 66.22 | 66.18 |

TABLE 1-continued $$A-X+\underset{R^2}{\overset{R^1}{C}}\!\!)_n\!\!-\!\!\underset{}{\bigcirc}\!\!-\!\!OCH_2CH_2F \quad (I)$$

$$\underset{R^4}{\overset{R^3}{\bigcirc}}\!\!\!\!\!-\!(O)_{\overline{p}}\!\!\underset{R^6}{\overset{R^5}{C}}\!\!(CH_2)_{\overline{m}}\!\!-\!\!A \quad (II)$$

| Compound No. | R¹ | R² | X | n | R³ | R⁴ | R⁵ | R⁶ | p | m | Position of FCH₂CH₂O— | Physical constants | | |
|---|---|---|---|---|---|---|---|---|---|---|---|---|---|---|
| | | | | | | | | | | | | H 5.88 | | 5.99 |
| | | | | | | | | | | | | F 12.32 | | 12.10 |
| 74 | — | — | O | 0 | 4-CH₃O— | H | H | H | 0 | 0 | 4- | C₁₆H₁₇FO₃ | | |
| | | | | | | | | | | | | | Calculated (%) | Found (%) |
| | | | | | | | | | | | | C | 69.55 | 69.80 |
| | | | | | | | | | | | | H | 6.20 | 6.31 |
| | | | | | | | | | | | | F | 6.88 | 6.53 |
| | | | | | | | | | | | | $\delta^{CCl_4}_{TMS}$(ppm): 3.69(s,3H), 4.80(s,2H),3.78–3.92(m,1H), 4.02–4.15(m,1H),4.23–4.34 (m,1H),4.70–4.82(m,1H), 6.54–7.26(m,8H) | | |
| 75 | — | — | O | 0 | 2-Cl— | 4-Cl— | H | H | 0 | 0 | 3- | $\eta_D^{20.3}$ = 1.5806 | | |
| | | | | | | | | | | | | C₁₅H₁₃Cl₂FO₂ | | |
| | | | | | | | | | | | | | Calculated (%) | Found (%) |
| | | | | | | | | | | | | C | 57.16 | 57.23 |
| | | | | | | | | | | | | H | 4.16 | 4.25 |
| | | | | | | | | | | | | Cl | 22.50 | 22.30 |
| | | | | | | | | | | | | F | 6.03 | 6.06 |
| 76 | — | — | O | 0 | 2-Cl— | 6-Cl— | H | H | 0 | 0 | 4- | m.p. = 68.6–67.7° C. | | |
| | | | | | | | | | | | | C₁₅H₁₃Cl₂FO₂ | | |
| | | | | | | | | | | | | | Calculated (%) | Found (%) |
| | | | | | | | | | | | | C | 57.16 | 57.31 |
| | | | | | | | | | | | | H | 4.16 | 4.19 |
| | | | | | | | | | | | | Cl | 22.50 | 22.40 |
| | | | | | | | | | | | | F | 6.03 | 6.11 |
| 77 | H | H | O | 1 | 4-Cl— | H | CH₃ | CH₃ | 1 | 1 | 4- | $\eta_D^{19.9}$ = 1.5405 | | |
| | | | | | | | | | | | | C₁₉H₂₂ClFO₃ | | |
| | | | | | | | | | | | | | Calculated (%) | Found (%) |
| | | | | | | | | | | | | C | 64.67 | 64.52 |
| | | | | | | | | | | | | H | 6.29 | 6.34 |
| | | | | | | | | | | | | Cl | 10.05 | 10.03 |
| | | | | | | | | | | | | F | 5.39 | 5.35 |
| 78 | — | — | O | 0 | 4-Cl— | H | H | H | 1 | 1 | 4- | m.p. = 121–122° C. | | |
| | | | | | | | | | | | | C₁₆H₁₆ClFO₃ | | |
| | | | | | | | | | | | | | Calculated (%) | Found (%) |
| | | | | | | | | | | | | C | 65.19 | 65.23 |
| | | | | | | | | | | | | H | 5.47 | 5.43 |
| | | | | | | | | | | | | Cl | 12.03 | 12.00 |
| | | | | | | | | | | | | F | 6.45 | 6.72 |
| 79 | — | — | O | 0 | 4-Cl— | H | H | H | 1 | 0 | 4- | m.p. = 60–60.7° C. | | |
| | | | | | | | | | | | | C₁₅H₁₄ClFO₃ | | |
| | | | | | | | | | | | | | Calculated (%) | Found (%) |
| | | | | | | | | | | | | C | 60.71 | 60.53 |
| | | | | | | | | | | | | H | 4.76 | 4.78 |
| | | | | | | | | | | | | Cl | 11.95 | 11.99 |
| | | | | | | | | | | | | F | 6.40 | 6.48 |
| 80 | H | H | O | 1 | 4-Cl— | H | H | H | 1 | 0 | 4- | m.p. = 60.7–61.6° C. | | |
| | | | | | | | | | | | | C₁₆H₁₆ClFO₃ | | |
| | | | | | | | | | | | | | Calculated (%) | Found (%) |
| | | | | | | | | | | | | C | 65.19 | 65.25 |
| | | | | | | | | | | | | H | 5.47 | 5.37 |
| | | | | | | | | | | | | Cl | 12.03 | 12.15 |
| | | | | | | | | | | | | F | 6.45 | 6.47 |
| 81 | H | H | O | 1 | 4-C(CH₃)₂CHO | H | H | H | 0 | 0 | 4- | $\eta_D^{20.0}$ = 1.5414 | | |
| | | | | | | | | | | | | C₁₉H₂₃FO₃ | | |
| | | | | | | | | | | | | | Calculated (%) | Found (%) |
| | | | | | | | | | | | | C | 71.67 | 71.85 |

TABLE 1-continued $$A-X \left( \underset{R^2}{\overset{R^1}{C}} \right)_n \text{—} \phi \text{—} OCH_2CH_2F \quad (I)$$

$$R^3 \text{—} \phi \text{—} (O)_p \underset{R^6}{\overset{R^5}{C}} (CH_2)_m A \quad (II)$$
(with $R^4$ on ring)

| Compound No. | R¹ | R² | X | n | R³ | A R⁴ | R⁵ | R⁶ | p | m | Position of FCH₂CH₂O— | Physical constants |
|---|---|---|---|---|---|---|---|---|---|---|---|---|
| | | | | | | | | | | | | H 7.28 7.31 |
| | | | | | | | | | | | | F 5.97 5.64 |
| 82 | H | H | O | 1 | 3-CH₂FCH₂O— | H | H | H | 0 | 0 | 3- | m.p. = 58.5–60.5° C. $C_{18}H_{20}F_2O_3$ |
| | | | | | | | | | | | | Calculated (%) / Found (%) |
| | | | | | | | | | | | | C 67.07 / 67.34 |
| | | | | | | | | | | | | H 6.25 / 6.11 |
| | | | | | | | | | | | | F 11.79 / 11.83 |
| 83 | H | H | O | 1 | 4-(CH₃)₂CHO— | H | H | H | 0 | 0 | 3- | $\eta_D^{20.0} = 1.5376$ $C_{19}H_{23}FO_3$ |
| | | | | | | | | | | | | Calculated (%) / Found (%) |
| | | | | | | | | | | | | C 71.67 / 71.55 |
| | | | | | | | | | | | | H 7.28 / 7.13 |
| | | | | | | | | | | | | F 5.97 / 5.99 |
| 84 | H | H | O | 1 | 4-CH₂FCH₂O— | H | H | H | 0 | 0 | 4- | m.p. = 62.5–64.8° C. $C_{18}H_{20}F_2O_3$ |
| | | | | | | | | | | | | Calculated (%) / Found (%) |
| | | | | | | | | | | | | C 67.07 / 67.31 |
| | | | | | | | | | | | | H 6.25 / 6.22 |
| | | | | | | | | | | | | F 11.79 / 11.85 |
| 85 | H | H | O | 1 | 2-CH₂FCH₂O— | H | H | H | 0 | 0 | 2- | m.p. = 71–72° C. $C_{18}H_{20}F_2O_3$ |
| | | | | | | | | | | | | Calculated (%) / Found (%) |
| | | | | | | | | | | | | C 67.07 / 67.00 |
| | | | | | | | | | | | | H 6.25 / 6.33 |
| | | | | | | | | | | | | F 11.79 / 11.84 |
| 86 | H | H | O | 1 | 4-CH₂FCH₂S— | H | H | H | 0 | 0 | 4- | $\eta_D^{20.6} = 1.5688$ $C_{18}H_{20}F_2O_2S$ |
| | | | | | | | | | | | | Calculated (%) / Found (%) |
| | | | | | | | | | | | | C 63.89 / 63.95 |
| | | | | | | | | | | | | H 5.96 / 5.68 |
| | | | | | | | | | | | | F 11.23 / 11.31 |
| | | | | | | | | | | | | S 9.48 / 9.55 |
| 87 | H | H | O | 1 | 4-Cl— | H | H | H | 0 | 0 | 2- | $\eta_D^{20.7} = 1.5568$ $C_{16}H_{16}ClFO_2$ |
| | | | | | | | | | | | | Calculated (%) / Found (%) |
| | | | | | | | | | | | | C 65.19 / 65.31 |
| | | | | | | | | | | | | H 5.47 / 5.39 |
| | | | | | | | | | | | | Cl 12.03 / 11.95 |
| | | | | | | | | | | | | F 6.45 / 6.54 |
| 88 | H | H | O | 1 | 4-Cl— | H | H | H | 0 | 0 | 3- | $\eta_D^{20.9} = 1.5572$ $C_{16}H_{16}ClFO_2$ |
| | | | | | | | | | | | | Calculated (%) / Found (%) |
| | | | | | | | | | | | | C 65.19 / 65.34 |
| | | | | | | | | | | | | H 5.47 / 5.35 |
| | | | | | | | | | | | | Cl 12.03 / 12.14 |
| | | | | | | | | | | | | F 6.45 / 6.36 |
| 89 | H | H | O | 1 | 4-Cl— | H | H | H | 0 | 0 | 4- | m.p. = 43–43.7° C. $C_{16}H_{16}ClFO_2$ |
| | | | | | | | | | | | | Calculated (%) / Found (%) |
| | | | | | | | | | | | | C 65.19 / 64.93 |
| | | | | | | | | | | | | H 5.43 / 5.36 |
| | | | | | | | | | | | | Cl 12.03 / 11.85 |
| | | | | | | | | | | | | F 6.45 / 6.54 |
| 90 | H | H | O | 1 | 3-Cl— | 4-Cl— | H | H | 0 | 0 | 4- | m.p. = 32.7–33.8° C. $C_{16}H_{15}Cl_2FO_2$ |
| | | | | | | | | | | | | Cal- Found |

TABLE 1-continued

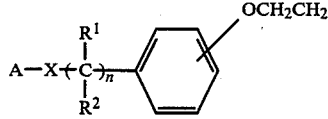 (I)

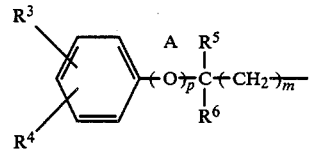 (II)

| Compound No. | $R^1$ | $R^2$ | X | n | A $R^3$ | $R^4$ | $R^5$ | $R^6$ | p | m | Position of $FCH_2CH_2O-$ | Physical constants |
|---|---|---|---|---|---|---|---|---|---|---|---|---|
| 91 | H | H | O | 1 | 2-Cl— | 4-Cl— | H | H | 0 | 0 | 4- | Calculated (%) / Found (%): C 58.37/58.18, H 4.59/4.62, Cl 21.54/21.39, F 5.77/5.85; m.p. = 49.5–50.4° C.; $C_{16}H_{15}Cl_2FO_2$ |
| 92 | H | H | O | 1 | 2-Cl— | 6-Cl— | H | H | 0 | 0 | 4- | Calculated (%) / Found (%): C 58.37/58.25, H 4.59/4.35, Cl 21.54/21.63, F 5.77/5.56; m.p. = 86.7–87.1° C.; $C_{16}H_{15}Cl_2FO_2$ |
| 93 | H | H | O | 1 | 4-CH(CH₃)₂ — | H | H | H | 0 | 0 | 4- | Calculated (%) / Found (%): C 58.37/58.44, H 5.49/4.71, Cl 21.54/21.34, F 5.77/5.84; $\eta_D^{18.5} = 1.5403$; $C_{19}H_{23}FO_2$ |
| 94 | H | H | O | 1 | 4-CH(CH₃)₂ — | H | H | H | 0 | 0 | 3- | Calculated (%) / Found (%): C 75.47/75.38, H 7.67/7.58, F 6.28/6.33; $\eta_D^{20.1} = 1.5392$; $C_{19}H_{23}FO_2$ |
| 95 | H | H | O | 1 | 4-CH₃— | H | H | H | 0 | 0 | 4- | Calculated (%) / Found (%): C 75.74/75.56, H 7.67/7.60, F 6.28/6.41; m.p. = 41.0–42.0° C.; $C_{17}H_{19}FO_2$ |
| 96 | H | H | O | 1 | 4-CH₃— | H | H | H | 0 | 0 | 3- | Calculated (%) / Found (%): C 74.43/74.52, H 6.98/6.83, F 6.93/6.95; $\eta_D^{19.9} = 1.5470$; $C_{17}H_{19}FO_2$ |
| 97 | H | H | O | 1 | 4-C₂H₅— | H | H | H | 0 | 0 | 4- | Calculated (%) / Found (%): C 74.43/74.66, H 6.98/7.01, F 6.93/6.67; $\eta_D^{19.6} = 1.5446$; $C_{18}H_{21}FO_2$ |
| 98 | H | H | O | 1 | 4-C₂H₅— | H | H | H | 0 | 0 | 3- | Calculated (%) / Found (%): C 74.97/74.83, H 7.34/7.22, F 6.58/6.54; $\eta_D^{19.7} = 1.5548$; $C_{18}H_{21}FO_2$; Calculated (%) / Found (%): C 94.97/74.75, H 7.34/7.51, F 6.58/6.53 |

TABLE 1-continued $$A-X+\overset{R^1}{\underset{R^2}{C}}_n-\text{Ph}-OCH_2CH_2F \quad (I)$$

$$\overset{R^3}{\underset{R^4}{\text{Ph}}}-(O)_p-\overset{R^5}{\underset{R^6}{C}}-(CH_2)_m- \quad (II)$$

| Compound No. | R¹ | R² | X | n | A R³ | R⁴ | R⁵ | R⁶ | p | m | Position of FCH₂CH₂O— | Physical constants |
|---|---|---|---|---|---|---|---|---|---|---|---|---|
| 99 | H | H | O | 1 | H | H | H | H | 0 | 0 | 4- | $\eta_D^{19.8} = 1.5515$ $C_{16}H_{17}FO_2$ C: Cal. 73.82, Found 73.97; H: 6.58, 6.60; F: 7.30, 7.56 |
| 100 | H | H | O | 1 | H | H | H | H | 0 | 0 | 3- | $\eta_D^{20.4} = 1.5508$ $C_{16}H_{17}FO_2$ C: 73.82, 74.01; H: 6.58, 6.76; F: 7.30, 7.41 |
| 101 | H | H | O | 1 | 4-Br— | H | H | H | 0 | 0 | 4- | m.p. = 58.4–59.2° C. $C_{16}H_{16}BrFO_2$ C: 56.65, 56.43; H: 4.76, 4.57; Br: 23.56, 23.81; F: 5.60, 5.67 |
| 102 | H | H | O | 1 | 4-Br— | H | H | H | 0 | 0 | 3- | $\eta_D^{20.7} = 1.5716$ $C_{16}H_{16}BrFO_2$ C: 56.65, 56.82; H: 4.76, 4.68; Br: 23.56, 23.44; F: 5.63, 5.85 |
| 103 | H | H | O | 1 | H | H | CH₃ | H | 0 | 0 | 4- | $\eta_D^{20.3} = 1.5425$ $C_{17}H_{19}FO_2$ C: 74.43, 74.45; H: 6.98, 7.02; F: 6.93, 6.95 |
| 104 | H | H | O | 1 | H | H | CH₃ | H | 0 | 0 | 3- | $\eta_D^{20.8} = 1.5451$ $C_{17}H_{19}FO_2$ C: 74.43, 74.48; H: 6.98, 6.97; F: 6.93, 6.95 |
| 105 | H | H | O | 1 | 4-CH₃O— | H | H | H | 0 | 0 | 4- | $\eta_D^{19.8} = 1.5580$ $C_{17}H_{19}FO_2$ C: 70.33, 70.35; H: 6.60, 6.72; F: 6.54, 6.38 |
| 106 | H | H | O | 1 | 3,4-CH₂$\langle$O—/O—$\rangle$ | H | H | H | 0 | 0 | 4- | $\eta_D^{20.0} = 1.5636$ $C_{17}H_{17}FO_4$ C: 67.10, 67.21; H: 5.63, 5.85; F: 6.24, 5.99 |
| 107 | CH₃ | H | O | 1 | H | H | H | H | 0 | 0 | 4- | $\eta_D^{18.2} = 1.5428$ $C_{17}H_{19}FO_2$ C: 74.43, 74.58; H: 6.98, 6.69; F: 6.93, 7.11 |

TABLE 1-continued $$A-X+C+_n-\text{C}_6\text{H}_4-\text{OCH}_2\text{CH}_2\text{F} \quad (I)$$

$$\text{(R}^3\text{)(R}^4\text{)C}_6\text{H}_3-(O)_p-C(R^5)(R^6)-(CH_2)_m-A \quad (II)$$

| Compound No. | R¹ | R² | X | n | R³ | R⁴ | R⁵ | R⁶ | p | m | Position of FCH₂CH₂O— | Physical constants |
|---|---|---|---|---|---|---|---|---|---|---|---|---|
| 108 | CH₃ | H | O | 1 | 4-CH₂FCH₂O— | H | CH₃ | H | 0 | 0 | 4- | $\eta_D^{18.1} = 1.5320$; C₂₀H₂₄F₂O₃; Calculated (%): C 68.55, H 6.90, F 10.85; Found (%): C 68.49, H 6.85, F 11.02 |
| 109 | H | H | O | 1 | 3-CH₃— | 4-CH₃— | H | H | 0 | 0 | 4- | $\eta_D^{18.2} = 1.5519$; C₁₈H₂₁FO₂; Calculated (%): C 74.97, H 7.34, F 6.58; Found (%): C 75.13, H 7.51, F 6.70 |
| 110 | H | H | O | 1 | 3-CH₃O— | 4-CH₃O— | H | H | 0 | 0 | 4- | m.p. = 73–74° C.; C₁₈H₂₁FO₄; Calculated (%): C 67.48, H 6.61, F 5.93; Found (%): C 67.54, H 6.63, F 5.95 |
| 111 | H | H | S | 1 | H | H | H | H | 0 | 0 | 4- | $\eta_D^{18.2} = 1.5867$; C₁₆H₁₇FOS; Calculated (%): C 69.53, H 6.20, F 6.87, S 11.60; Found (%): C 69.44, H 6.18, F 6.95, S 11.66 |
| 112 | H | H | O | 1 | 4-C₂H₅O— | H | H | H | 0 | 0 | 4- | $\eta_D^{18.3} = 1.5530$; C₁₈H₂₁FO₃; Calculated (%): C 71.03, H 5.96, F 6.24; Found (%): C 70.85, H 6.01, F 6.28 |
| 113 | H | H | O | 1 | 3-Cl— | 4-C₂H₅O— | H | H | 0 | 0 | 4- | $\eta_D^{18.2} = 1.5571$; C₁₈H₂₀ClFO₃; Calculated (%): C 63.81, H 5.95, Cl 10.47, F 5.61; Found (%): C 64.12, H 5.84, Cl 10.52, F 5.63 |
| 114 | CH₃ | CH₃ | O | 1 | 4-Cl— | H | H | H | 0 | 0 | 4- | $\eta_D^{19.8} = 1.5457$; C₁₈H₂₀ClFO₂; Calculated (%): C 66.97, H 6.25, Cl 10.98, F 5.89; Found (%): C 67.21, H 6.37, Cl 10.70, F 5.77 |
| 115 | CH₃ | CH₃ | O | 1 | 4-CH(CH₃)₂ | H | H | H | 0 | 0 | 4- | $\eta_D^{18.7} = 1.5421$; C₂₁H₂₇FO₂; Calculated (%): C 76.33, H 8.24, F 5.75; Found (%): C 76.53, H 8.37, F 5.50 |
| 116 | CH₃ | CH₃ | O | 1 | 4-CH₃O— | H | H | H | 0 | 0 | 3- | $\eta_D^{20.0} = 1.5571$; C₁₉H₂₃FO₃; Calculated (%): C 71.68, H 7.28; Found (%): C 71.59, H 7.32 |

TABLE 1-continued

| | | | | | | | OCH$_2$CH$_2$F (I) | | | | R$^3$ | | A R$^5$ | | | | (II) |
|---|---|---|---|---|---|---|---|---|---|---|---|---|---|---|---|---|---|

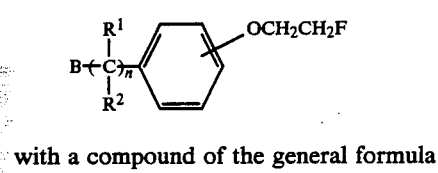

| Compound No. | R$^1$ | R$^2$ | X | n | R$^3$ | A R$^4$ | R$^5$ | R$^6$ | p | m | Position of FCH$_2$CH$_2$O— | Physical constants | |
|---|---|---|---|---|---|---|---|---|---|---|---|---|---|
| | | | | | | | | | | | F | 5.97 | 5.91 |

When in general formulae (I) and (II), R$^1$ and R$^2$ are not identical atoms or groups, and/or R$^5$ and R$^6$ are not identical atoms or groups, the compounds of this invention have an asymmetric carbon atom. Hence, the compounds of this invention include optical isomers ascribable to the asymmetric carbon atom and mixtures thereof.

The 2-fluoroethoxy-substituted benzene derivative of this invention represented by general formula (I) can be produced by reacting a compound of the general formula

(III)

with a compound of the general formula

A—D (IV).

In the above general formulae (III) and (IV), the symbols have the following meanings.

R$^1$ and R$^2$ represent a hydrogen atom or a lower alkyl group.

n represents 0 or 1.

A is a group of the general formula

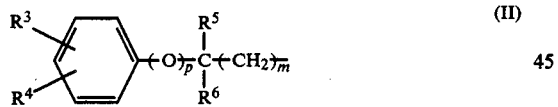

(II)

wherein R$^3$ and R$^4$ represent a hydrogen atom, a halogen atom, a lower alkyl group, a lower alkoxy group, a lower alkylthio group, a lower haloalkoxy group, a lower haloalkylthio group or a methylenedioxy group, R$^5$ and R$^6$ represent a hydrogen atom or a lower alkyl group, and p and m represent 0 or 1.

One of B and D is a halogen atom and the other is a group represented by the general formula

—X—M wherein X represents an oxygen or sulfur atom, and M represents a hydrogen atom, an alkali metal atom, or an alkaline earth metal atom; provided that when n is 0, B is a group of the general formula —X—M, and D is a halogen atom.

Some of the compounds of general formula (III) can be produced by a method schematically shown below from hydroxybenzaldehyde or a hydroxybenzoic acid ester and 1-chloro-2-fluoroethane, for example.

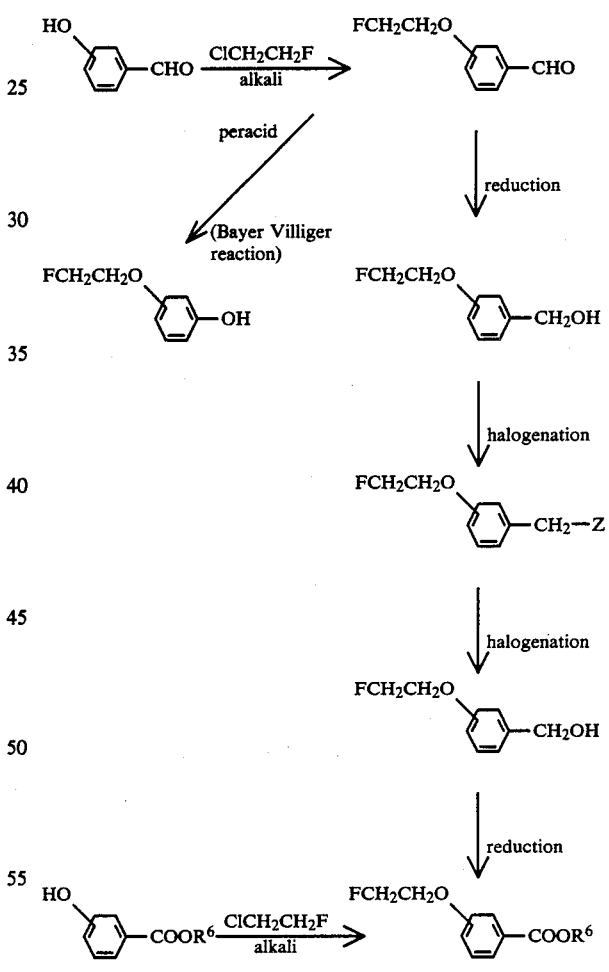

Some other compounds of general formula (III) can be produced in accordance with the following route.

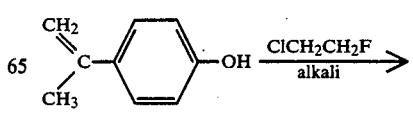

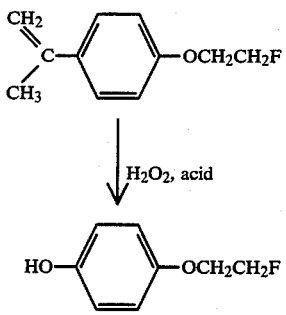

The process of this invention differs in the mode of practice depending upon whether the starting compound of general formula (III) or (IV) is an alcohol (phenol) or thiol (thiophenol) (i.e., M is a hydrogen atom in the above formula), or an alcoholate (i.e., M is an alkali metal atom or an alkaline metal atom in the above formula).

When an alcohol (phenol) or thiol (thiophenol) in which M is a hydrogen atom is to be reacted with the halide, the reaction is carried out at a temperature of 20° to 180° C., preferably 30° to 140° C. in a suitable solvent in the presence of a base as an acid binder to produce the desired 2-fluoroethoxy-substituted benzene derivative of general formula (I). The base herein denotes an oxide, hydroxide, carbonate, etc. of an alkali metal or an alkaline earth metal, or an amine such as triethylamine. Examples are potassium carbonate, barium oxide and sodium hydroxide. Examples of the solvent that can be used in this process include water; aromatic hydrocarbons such as benzene and toluene; aliphatic hydrocarbons such as hexane and heptane; halogenated hydrocarbons such as chloroform and dichloromethane; aprotic polar solvents such as dimethylformamide, dimethyl sulfoxide and 1,3-dimethyl-2-imidazolidinone; ethers such as diethyl ether, dioxane, and tetrahydrofuran; and nitriles such as acetonitrile and propionitrile. Phase transfer catalysts typified by tetra-n-butylammonium bromide and triethylbenzylammonium chloride are suitably used as a catalyst.

When an alcoholate in which M is an alkali metal atom or an alkaline earth metal atom is to be reacted with the halide, the reaction is carried out at 20° to 180° C., preferably 30° to 140° C., in a solvent. The above-exemplified solvents excepting water can be used in this process, too.

After the reaction, the reaction mixture is poured into water and extracted with a solvent such as toluene and ethyl acetate. By evaporating off the solvent and low-boiling compounds from the extract, the compound of formula (I) can be isolated. The product as isolated can be directly used as an insecticide or an acaricide. By further purifying it by distillation or recrystallization, it can be used alone as an agricultural chemical.

The acaricidal and insecticidal agent of this invention contains the compound of general formula (I) as an active ingredient.

For use in combatting acarids and insect pests, the compound of general formula (I) may be used singly. In order to make it easy to use as a pest controlling agent, it is the general practice to formulate it into a preparation together with a carrier, and apply it optionally after dilution. Formulation does not require any special conditions, and it can be formulated into any desired form such as an emulsifiable concentrate, a wettable powder, a dust, granules, an oil, an aerosol, etc. by methods well known to those skilled in the art in the production of general agricultural chemicals, and used in the desired applications.

The acaridical and insecticidal agent of this invention usually contains 0.001 to 95% by weight, preferably 0.01 to 50% by weight, of the compound of general formula (I).

Multi-purpose compositions having better efficacy can be prepared by mixing the acaricidal and insecticidal agent of this invention with other biologically active substances, such as organophosphorus insecticides, carbamate insecticides, pyrethroid insecticides, other insecticides, acaricides, fungicides, nematocides, herbicides, and other agricultural chemicals. The synergistic effect by such mixing can also be expected.

The organophosphorus insecticides include, for example, pyridaphenthion(O,O-diethyl 2,3-dihydro-3-oxo-2-phenyl-6-pyridazinyl phosphorothionate), dichlorvos(2,2-dichlorovinyl O,O-dimethyl phosphate), fenitrothion(O,O-dimethyl O-(3-methyl-4-nitrophenyl)-phosphorothionate, diazinon[O,O-diethyl O-(2-isopropyl-6-methyl-4-pyrimidinyl phosphorothionate], cyanophos[O-(4-cyano-phenyl)O,O-dimethyl phosphorothionate], phenthoate{S-[α-(ethoxycarbonyl)benzyl]O,O-dimethyl phosphorothiorothionate}, salithion(2-methoxy-4H-1,3,2-benzodioxaphosphorin 2-sulfide), cyanofenphos[O-(4-cyanophenyl)O-ethyl phenyl phosphorothionate], fenthion[O,O-dimethyl O-(3-methyl-4-methylthiophenyl)phosphorothionate], chloropyrifos-[O-(3,5,6-trichloro-2-pyridyl)O,O-diethyl phosphorothionate], dimethoate[O,O-dimethyl S-(N-methylcarbamoylmethyl phosphorothiolothionate], malathion[S-1,2-bis(ethoxycarbonyl)ethyl O,O-dimethyl phosphorothiolothionate], acephate(O,S-dimethyl N-acetylphosphoramidothiolate), and dialifos[S-(2-chloro-1-phthalimidoethyl)O,O-diethyl phosphorothiolothionate].

The carbamate insecticides include, for example, carbaryl(1-naphthyl N-methylcarbamate), MTMC(m-tolyl N-methylcarbamate), pirimicarb(2-dimethylamino-5,6-dimethylpyrimidin-4-yl dimethylcarbamate), MPMC(3,4-xylyl N-methylcarbamate), propoxur(O-isopropoxyphenyl N-methylcarbamate), and aldicarb(2-methyl-2-methylthiopropionaldehyde O-methytl-carbamoyloxime).

The pyrethroid insecticides include, for example, allethrin[d,l-(3-allyl-2-methyl-2-cyclopentene-4-one-1-yl)chrysanthemate], tetramethrin[N-(3,4,5,6-tetrahydrophthalimido)methyl chrysanthemate], resmethrin(5-benzyl-3-furylmethyl-d,l-cis,trans-chrysanthemate), phenothrin(3-phenoxybenzyl d,l-cis,trans-chrysanthemate), furamethrin[(5-propargyl)furfuryl d,l-cis,trans-chrysanthemate], permethrin[3-phenoxybenzyl d,l-cis,-trans-3-(2,2-dichlorovinyl)-2,2-dimethylcyclopropanecarboxylate], cypermethrin[1-cyano-3-phenoxybenzyl d,l-cis,trans-3-(2,2-dichlorovinyl-2,2-dimethylcyclopropanecarboxylate], decamethrin[l-cyano-3-phenoxybenzyl d,l-cis-3-(2,2-dibromovinyl)-2,2-dimethylcyclopropanecarboxylate], fenvalerate[α-cyano-3-phenoxybenzyl α-isopropyl-4-chlorophenyl acetate], and fenpropathrin(α-cyano-3-phenoxybenzyl 2,2,3,3-tetramethylcyclopropanecarboxylate).

The other insecticides and acaricides include, for example, tetradifon(4-chlorophenyl 2′,4′,5′-trichlorophenylsulfone), dicofol[2,2,2-trichloro-1,1-bis(4-chlorophenyl)ethanol], amitraz[3-methyl-1,5-bis(2,4- xylyl)-1,3,5-triazapenta-1,4-diene], chlorobenzilate(ethyl 4,4'-dichlorobenzilate), BCPE[1,1-bis(4-chlorophenyl)ethanol], benzomate(ethyl O-benzoyl 3-chloro-2,6-dimethoxybenzohydroximinate), chlorodimeform[N'-(4-chloro-2-tolyl)-N,N-dimethylformamidine], diflubenzuron[1-(4-chlorophenyl)-3-(2,6-difluorobenzoyl)urea], and [3-phenoxybenzyl 2-(4-ethoxyphenyl)-2-methyl propyl ether].

The compounds of this invention have high stability to light, heat, oxidation, etc. As required, however, more stable compositions of the compounds of this invention may be obtained by adding suitable amounts of antioxidants or ultraviolet absorbers, for example phenol derivatives such as BHT(2,6-di-tert-butyl-p-cresol) and BHA(a mixture of 2-tert-butyl-4-methoxyphenol and 3-tert-butyl-4-methoxyphenol), biphenol derivatives, arylamines such as phenyl-α-naphthylamine, phenyl-β-naphthylamine or a condensate of phenetidine and acetone, or benzophenone compounds.

The following Examples, Test Examples and Referential Examples illustrate the present invention in more detail.

REFERENTIAL EXAMPLE 1

This example illustrates the synthesis of 4-(2-fluoroethoxy)benzyl chloride, a starting material.

4-Hydroxybenzaldehyde (26.0 g), 20.7 g of 1-fluoro-2-chloroethane and 42.4 g of anhydrous potassium carbonate were added to 100 ml of dimethylformamide, and reacted at 130° C. for 5 hours. After the reaction, the reaction mixture was cooled to room temperature, poured into water, and then extracted with toluene. The toluene layer was washed with water, and dried over anhydrous sodium sulfate. Toluene was evaporated under reduced pressure to give 35.6 g of crude 4-(2-fluoroethoxy)benzaldehyde.

The crude 4-(2-fluoroethoxy)benzaldehyde (35.6 g) was dissolved in 140 ml of ethanol, and 11.0 g of sodium borohydride was carefully added to the solution at 47° to 50° C. After adding sodium borohydride, the reaction was carried out at 50° C. for 2 hours. After the reaction, the reaction mixture was cooled to room temperature and water was added. The mixture was extracted with toluene. The toluene layer was washed with water and dried over anhydrous sodium sulfate. Toluene was evaporated under reduced pressure to give 32.4 g of 4-(2-fluoroethoxy)benzyl alcohol as crystals (m.p. 37.3°–38.0° C.).

The crystals were dissolved in 100 ml of benzene, and 26.1 g of thionyl chloride was added at less than 40° C. The reaction was further carried out at room temperature for 2 hours. The reaction mixture was poured into water and extracted with toluene. The toluene layer was washed with a cooled saturated aqueous solution of sodium hydrogen carbonate and then with water, and dried over anhydrous sodium sulfate. Toluene was evaporated under reduced pressure to give 31.2 g of 4-(2-fluoroethoxy)benzyl chloride as an oil.

$\delta_{TMS}^{CCl4}$ (ppm): 4.38 (s, 2H), 3.72–3.80 (m, 1H), 4.00–4.08 (m, 1H), 4.23–4.30 (m, 1H), 4.71–4.78 (m, 1H), 6.73 (d, 2H), 7.17 (d, 2H).

REFERENTIAL EXAMPLE 2

This example illustrates the synthesis of 3-(2-fluoroethoxy)benzyl chloride, a starting material.

Thirty grams of ethyl 3-hydroxybenzoate, 14.9 g of 1-fluoro-2-chloroethane and 37.4 g of anhydrous potassium carbonate were added to 130 ml of dimethylformamide. With stirring, the reaction was carried out at 120° C. for 4 hours. The reaction mixture was cooled to room temperature, poured into water, and extracted with toluene. The toluene layer was washed with water, and dried over anhydrous sodium sulfate. Toluene was evaporated under reduced pressure to give 32.6 g of crude ethyl 3-(2-fluoroethoxy)benzoate. The resulting crude ethyl 3-(2-fluoroethoxy)benzoate (32.6 g) was added at 40° to 45° C. to a solution of 6.0 g of lithium aluminum hydride in 200 ml of dry tetrahydrofuran, and the mixture was heated under reflux for 2 hours. After the reaction, the reaction mixture was cooled to room temperature. Ethanol and water in this order were added to the mixture to decompose the unreacted lithium aluminum hydride. Water was then added, and the mixture was extracted with toluene. The toluene layer was washed with water, and dried over anhydrous sodium sulfate. Toluene was removed to give 26.0 g of crude 3-(2-fluoroethoxy)benzyl alcohol This compound was chlorinated to give 30.0 g of 3-(2-fluoroethoxy)benzyl chloride.

$\delta_{TMS}^{CCl4}$ (ppm): 4.47 (s, 2H), 3.97–4.06 (m, 1H), 4.22–4.31 (m, 1H), 4.37–4.50 (m, 1H), 4.84–4.95 (m, 1H), 6.71–7.26 (m, 4H).

REFERENTIAL EXAMPLE 3

This example illustrates the synthesis of 4-(2-fluoroethoxy)phenol, a starting material.

To 30 ml of dimethylformamide were added 7.0 g of 4-isopropenylphenol, 6.1 g of 1-fluoro-2-chloroethane and 8.7 g of potassium carbonate. With stirring, they were reacted at 120° C. for 4 hours. The reaction mixture was cooled to room temperature, and poured into water. The mixture was then extracted with toluene. The toluene layer was washed with water and dried over anhydrous sodium sulfate. Toluene was evaporated under reduced pressure to give 9.0 g of crude 4-(2-fluoroethoxy)isopropenylbenzene.

$\delta_{TMS}^{CCl4}$ (ppm): 2.08 (s, 3H), 3.9–4.0 (m, 1H), 4.1–4.3 (m, 1H), 4.3–4.4 (m, 1H), 4.75–4.95 (m, 2H), 5.16 (s, 1H), 6.72 (d, 2H), 7.26 (d, 2H).

Then, a mixture of 30 ml of methanol and 2 ml of concentrated sulfuric acid was warmed to 40° C., and 9.0 g of the resulting crude 4-(2-fluoroethoxy)-isopropenylbenzene prepared as above and a 30% aqueous solution of hydrogen peroxide were separately added dropwise to the warmed mixture over the course of 20 minutes. The reaction was continued for 1 hour. The reaction mixture was cooled, poured into water, and extracted with toluene. The toluene layer was washed with water, and dried over anhydrous sodium sulfate. Toluene was evaporated under reduced pressure to give 7.3 g of crude 4-(2-fluoroethoxy)phenol. The resulting crude phenol was recrystallized to give 6.8 g of pure 4-(2-fluoroethoxy)phenol as crystals.

$\delta_{TMS}^{CDCl3}$ (ppm): 3.98–4.06 (m, 1H), 4.25–4.34 (m, 1H) 4.45–4.54 (m, 1H), 4.93–5.01 (m, 1H), 4.65–5.04 (broad, 1H), 6.82 (s, 4H).

EXAMPLE 1

This example illustrates the synthesis of 3-(2-fluoroethoxy)benzyl-2-(4-chlorophenyl)-2-methylpropyl ether (compound No. 1).

A mixture consisting of 2.0 g of 3-(2-fluoroethoxy)benzyl chloride, 2.3 g of 2-(4-chlorophenyl)-2-methylpropyl alcohol, 0.5 g of triethylbenzylammonium bromide and 5 g of a 50% aqueous solution of sodium hydroxide was stirred at 50° C. for 2 hours. The reaction mixture was cooled to room temperature, and poured into water. Toluene was added, and the mixture was fully stirred. The toluene layer was separated, washed with water and dried over anhydrous sodium sulfate. Toluene was evaporated under reduced pressure. The resulting crude ether was purified by silica gel (100 g) column chromatography (developing solvent: toluene) to give 2.9 g of the desired 3-(2-fluoroethoxy)benzyl 2-(4-chlorophenyl)-2-methylpropyl ether.

$[n]_D^{19.5}$: 1.5453

$v_{max}^{film}$ (cm$^{-1}$): 2885, 2835, 1590, 1500, 1455, 1275, 1105, 1020, 970, 790, 750, 710.

$\delta_{TMS}^{CCl_4}$ (ppm): 1.30 (s, 6H), 3.31 (s, 2H), 4.34 (s, 2H), 3.82-3.91 (m, 1H), 4.09-4.17 (m, 1H), 4.32-4.42 (m, 1H), 4.80-4.89 (m, 1H), 6.60-7.29 (m, 8H).

EXAMPLE 2

This example illustrates the synthesis of 4-(2-fluoroethoxy)benzyl 2-phenyl-2-methylpropyl ether (compound No. 35).

Sodium hydride (1.4 g; 60% in oil) was added to 20 ml of dry acetonitrile, and a solution of 4.4 g of 2-phenyl-2-methylpropyl alcohol in 10 ml of acetonitrile was added dropwise at 50° C. The mixture was heated under reflux for 30 minutes, and a solution of 5.4 g of 4-(2-fluoroethoxy)benzyl chloride in 10 ml of acetonitrile was added dropwise over 10 minutes. The mixture was further heated under reflux for 1 hour. The reaction mixture was cooled to room temperature, poured into water, and extracted with toluene. The toluene layer was washed with water and dried over anhydrous sodium sulfate. Toluene was evaporated under reduced pressure. The resulting crude ether was purified by silica gel (180 g) column chromatography (developing solvent: a 2:1 mixture of toluene and n-hexane) to give 6.5 g of 4-(2-fluoroethoxy)benzyl 2-phenyl-2-methylpropyl ether.

$[n]_D^{19.8}$: 1.5392

$v_{max}^{film}$ (cm$^{-1}$): 2880, 2840, 1610, 1515, 1255, 1090-1100, 925, 770, 700.

$\delta_{TMS}^{CCl_4}$ (ppm): 1.32 (s, 6H), 3.33 (s, 2H), 4.31 (s, 2H), 3.85-3.96 (m, 1H), 4.12-4.21 (m, 1H), 4.28-4.39 (m, 1H), 4.77-4.86 (m, 1H), 6.66-7.34 (m, 9H).

EXAMPLE 3

This example illustrates the synthesis of 4-(2-fluoroethoxy)benzyl 2-(4-methylphenyl)-2-methylpropyl ether (compound No. 38).

Sodium hydride (0.9 g; 60% in oil) was added to 20 ml of toluene, and with heating, a solution of 2.5 g of 2-(4-methylphenyl)-2-methylpropyl alcohol in 10 ml of a mixture of 25% dimethylformamide and toluene was added dropwise over the course of 15 minutes. The mixture was stirred for 10 minutes, and then a solution of 2.9 g of 4-(2-fluoroethoxy)benzyl chloride in 10 ml of toluene was added dropwise over the course of 20 minutes. The mixture was further heated under reflux for 1 hour. The reaction mixture was cooled to room temperature, poured into water, and then extracted with toluene. The toluene layer was washed with water and dried over anhydrous sodium sulfate. Toluene was evaporated under reduced pressure. The resulting crude ether was purified by silica gel (100 g) column chromatography (developing solvent: a 2:1 mixture of toluene and n-hexane) to give 3.3 g of the desired 4-(2-fluoroethoxy)benzyl 2-(4-methylphenyl)-2-methylpropyl ether.

$[n]_D^{20.4}$: 1.5374

$v_{max}^{film}$ (cm$^{-1}$): 2880, 2840, 1615, 1515, 1250, 1090, 930, 815.

$\delta_{TMS}^{CCl_4}$ (ppm): 1.32 (s, 6H), 4.32 (s, 2H), 2.27 (s, 3H), 6.63-7.22 (m, 8H), 3.33 (s, 2H), 3.77-3.84 (m, 1H), 4.04-4.13 (m, 1H), 4.23-4.32 (m, 1H), 4.67-4.79 (m, 1H).

EXAMPLE 4

This example illustrates the synthesis of 4-(2-fluoroethoxy)benzyl 3,4-methylenedioxybenzyl ether (compound No. 62).

A mixture composed of 1.0 g of 4-(2-fluoroethoxy)phenol, 1.3 g of 3,4-methylenedioxybenzyl chloride, 0.3 g of triethylbenzylammonium bromide and 20 g of a 50% aqueous solution of potassium hydroxide was stirred at 30° C. for 4 hours. The reaction mixture was cooled to room temperature, and poured into water. Toluene was added to the mixture, and the mixture was fully stirred. The toluene layer was then separated, washed with water, and dried over anhydrous sodium sulfate. Toluene was evaporated under reduced pressure. The resulting crude ether was purified by recrystallization from benzene to give 1.15 g of the desired ether.

m.p.: 81.5°-82.2° C.

$v_{max}^{film}$ (cm$^{-1}$): 1505, 1445, 1395, 1265, 1225, 1045, 1010, 925, 830, 785, 755.

$\delta_{TMS}^{CCl_4}$ (ppm): 3.82-3.90 (m, 1H), 4.07-4.16 (m, 1H), 4.27-4.36 (m, 1H), 4.76-4.85 (m, 1H), 4.79 (s, 2H), 5.88 (s, 2H), 6.55-6.92 (m, 7H).

EXAMPLE 5

This example illustrates the synthesis of 3-(2-fluoroethoxy)phenyl 3,4-dichlorobenzyl ether (compound No. 65).

Sodium hydride (0.19 g; 60%) was added to 20 ml of dry 1,3-dimethyl-2-imidazolidinone (to be referred to as DMI), and then 0.7 g of 3-(2-fluoroethoxy)phenol dissolved in DMI was added dropwise at 50° C. The mixture was stirred at 70° C. for 30 minutes. Then, a solution of 0.9 g of 3,4-dichlorobenzyl chloride in 5 ml of DMI was added dropwise over the course of 10 minutes. Furthermore, the mixture was stirred at 70° C. for 1.5 hours. The reaction mixture was cooled to room temperature and poured into water. Toluene was added, and the mixture was fully stirred. The toluene layer was separated, and washed with water. The toluene layer was dried over anhydrous sodium sulfate, and under reduced pressure, toluene and low volatile components were evaporated to give 1.1 g of the desired ether.

$[n]_D^{21.0}$: 1.5801

$v_{max}^{film}$ (cm$^{-1}$): 1610, 1600, 1500, 1480, 1460, 1295, 1270, 1190, 1165, 1055, 1035, 890, 820, 775.

$\delta_{TMS}^{CCl_4}$ (ppm): 3.90-4.00 (m, 1H), 4.17-4.26 (m, 1H), 4.35-4.44 (m, 1H), 4.83-4.91 (m, 1H), 4.90 (s, 2H), 6.37-7.47 (m, 7H).

EXAMPLE 6

This example illustrates the synthesis of 4-(2-fluoroethoxy)phenyl 4-(2-fluoroethoxy)benzyl ether (compound No. 73).

Sodium hydride (0.20 g; 60%) was added to 20 ml of dry acetonitrile, and 0.7 g of 4-(2-fluoroethoxy)phenol dissolved in 5 ml of acetonitrile was added dropwis at 50° C. The mixture was heated under reflux at 50° C. for 30 minutes. Then, a solution of 1.0 g of 4-(2-fluoroethoxy)benzyl chloride in 5 ml of acetonitrile was added dropwise over 10 minutes. The mixture was heated under reflux for 1.5 hours. The reaction mixture was cooled to room temperature, poured into water, and extracted with ethyl acetate. The ethyl acetate layer was washed with water and dried over anhydrous sodium sulfate. Ethyl acetate was evaporated under reduced pressure. The resulting crude ether was recrystallized from benzene to give 1.08 g of the desired ether.

m.p.: 121.8°–123.0° C.

$\nu_{max}^{film}$ (cm$^{-1}$): 2930, 1615, 1590, 1505, 1450, 1385, 1235, 1180, 1115, 1080, 1050, 1015, 925, 880, 820, 810, 750.

$\delta_{TMS}^{CDCl_3}$ (ppm): 4.90 (s, 2H), 3.90–4.04 (m, 2H), 4.18–4.32 (m, 2H), 4.37–4.48 (m, 2H), 4.86–4.97 (m, 2H), 6.87 (s, 4H), 6.90 (d, 2H), 7.33 (d, 2H).

EXAMPLE 7

This example illustrates the synthesis of 4-(2-fluoroethoxy)benzyl 2-(4-chlorophenoxy)-2-methylpropyl ether (compound No. 77).

A mixture consisting of 1.0 g of 4-(2-fluoroethoxy)benzyl chloride, 1.0 g of 2-(4-chlorophenoxy)-2-methylpropyl alcohol, 0.3 g of triethylbenzylammonium bromide and 20 g of a 50% aqueous solution of sodium hydroxide was stirred at 50° C. for 2 hours. The reaction mixture was cooled to room temperature, and poured into water. Toluene was added, and the mixture was fully stirred. The toluene layer was separated, washed with water, and dried over anhydrous sodium sulfate. Toluene and low-volatile components were evaporated under reduced pressure to give 1.6 g of the desired 4-(2-fluoroethoxy)benzyl 2-(4-chlorophenoxy)-2-methylpropyl ether.

$[n]_D^{19.9}$: 1.5405

$\nu_{max}^{film}$ (cm$^{-1}$): 2980, 2940, 2855, 1615, 1595, 1520, 1490, 1245, 1160, 1100, 1060, 1020, 925, 900, 855, 830, 720.

$\delta_{TMS}^{CCl_4}$ (ppm): 1.24 (s, 6H), 3.27 (s, 2H), 4.37 (s, 2H), 3.82–3.92 (m, 1H), 4.08–4.17 (m, 1H), 4.26–4.34 (m, 2H), 4.74–4.83 (m, 1H), 6.72–7.20 (m, 8H).

EXAMPLE 8

This example illustrates the synthesis of 4-(2-fluoroethoxy)phenyl 2-(4-chlorophenyl)ethyl ether (compound No. 78).

To 30 ml of dry dimethylformamide were added 0.96 g of 1-(4-chlorophenoxy)-2-chloroethane, 0.7 g of 4-(2-fluoroethoxy)phenol and 1.5 g of anhydrous potassium carbonate, and the mixture was stirred at 130° C. for 3 hours. The mixture was cooled to room temperature and poured into water. Ethyl acetate was added, and the mixture was fully stirred. The ethyl acetate layer was separated and washed with water, and dried over anhydrous sodium sulfate. Ethyl acetate was evaporated under reduced pressure. The resulting crude ether was recrystallized from benzene to give 1.07 g of the desired ether.

m.p.: 121°–122° C.

$\nu_{max}^{film}$ (cm$^{-1}$): 2930, 1600, 1510, 1495, 1450, 1285, 1235, 1085, 1070, 1050, 940, 920, 890, 820, 750.

$\delta_{TMS}^{DHSO-D_6}$ (ppm): 4.22 (s, 4H), 3.91–4.0 (m, 1H), 4.19–4.28 (m, 1H), 4.39–4.47 (m, 1H), 4.87–4.96 (m, 1H), 6.86 (s, 4H), 6.85 (d, 2H), 7.24 (d, 2H).

EXAMPLE 9

This example illustrates the synthesis of 4-(2-fluoroethoxy)phenyl 4-chlorophenoxymethyl ether (compound No. 79).

Sodium hydride (0.28 g; 60%) was added in 30 ml of dry tetrahydrofuran, and thereafter, 1.0 g of 4-(2-fluoroethoxy)phenol dissolved in 5 ml of tetrahydrofuran was added dropwise at 40° C. The mixture was heated under reflux for 30 minutes, and a solution of 1.23 g of 4-chlorophenoxychloromethane in 5 ml of tetrahydrofuran was added dropwise over the course of 10 minutes. The mixture was further heated under reflux for 2 hours. The reaction mixture was cooled to room temperature, poured into water and extracted with toluene. The toluene layer was washed with water, and dried over anhydrous sodium sulfate. Toluene was evaporated under reduced pressure. The residue was recrystallized from benzene to give 1.5 g of the desired ether.

m.p.: 60.0°–60.7° C.

$\nu_{max}^{film}$ (cm$^{-1}$): 2985, 2920, 1510, 1490, 1210, 1035, 925, 880, 820, 730.

$\delta_{TMS}^{CDCl_3}$ (ppm): 5.60 (s, 2H), 3.90–3.99 (m, 1H), 4.19–4.27 (m, 1H), 4.38–4.47 (m, 1H), 4.87–4.95 (m, 1H), 6.79–7.31 (m, 8H).

EXAMPLE 10

This example illustrates the synthesis of 4-(2-fluoroethoxy)benzyl 4-chlorophenoxymethyl ether (compound No. 80).

A mixture composed of 1.0 g of 4-chlorophenoxychloromethane, 1.0 g of 4-(2-fluoroethoxy)benzyl alcohol, 0.3 g of triethylbenzylammonium bromide and 20 g of a 50% aqueous solution of sodium hydroxide was stirred at 50° C. for 1.5 hours. The reaction mixture was cooled to room temperature, and poured into water. Toluene was added, and the mixture was fully stirred. The toluene layer was separated, washed with water, and dried over anhydrous sodium sulfate. Toluene was evaporated. The resulting crude ether was recrystallized from benzene to give 1.18 g of the desired 4-(2-fluoroethoxy)benzyl 4-chlorophenoxymethyl ether.

m.p.: 60.7°–61.6° C.

$\nu_{max}^{film}$ (cm$^{-1}$): 2980, 1620, 1580, 1500, 1270, 1255, 1230, 1185, 1170, 1080, 1010, 985, 895, 825.

$\delta_{TMS}^{CCl_4}$ (ppm): 4.54 (s, 2H), 5.10 (s, 2H), 3.89–3.97 (m, 1H), 4.14–4.24 (m, 1H), 4.32–4.41 (m, 1H), 4.79–4.89 (m, 1H), 6.70–7.18 (m, 8H).

EXAMPLE 11

This example illustrates the synthesis of 4-(2-fluoroethoxy)benzyl 4-chlorobenzyl ether (compound No. 89).

A mixture consisting of 5.3 g of 4-(2-fluoroethoxy)benzyl alcohol, 5.0 g of 4-chlorobenzyl chloride, 0.5 g of triethylbenzylammonium bromide and 20 g of a 50% aqueous solution of sodium hydroxide was stirred at 50° C. for 4 hours. The reaction mixture was cooled to room temperature, poured into water, and extracted with toluene. The toluene layer was washed with water, and dried over anhydrous sodium sulfate. Toluene was evaporated under reduced pressure. The resulting crude ether was purified by silica gel (200 g) column chromatography (developing solvent: benzene) to give 8.2 g of the desired 4-(2-fluoroethoxy)benzyl 4-chlorobenzyl ether as pale yellow crystals.

m.p.: 43.0°–43.7° C.

$\nu_{max}^{film}$ (cm$^{-1}$): 2835, 1615, 1495, 1455, 1365, 1305, 1250, 1180, 1070–1085, 1020, 930, 820.

$\delta_{TMS}^{CCl_4}$ (ppm): 3.79–3.90 (m, 1H), 4.05–4.19 (m, 1H), 4.26–4.37 (m, 1H), 4.72–4.84 (m, 1H), 4.35 (s, 4H), 6.75 (d, J=9.0, 2H), 7.15 (d, J=9.0, 2H), 7.19 (s, 4H).

EXAMPLE 12

This example illustrates the synthesis of 3-(2-fluoroethoxy)benzyl benzyl ether (compound No. 100).

Sodium hydride (0.24 g; 60% in oil) was suspended in 30 ml of dry tetrahydrofuran, and then 1.0 g of 3-(2-fluoroethoxy)benzyl alcohol was added. The mixture was stirred at 50° to 60° C. for 30 minutes, and 1.7 g of benzyl bromide was added. The mixture was heated under reflux for 3 hours. The reaction mixture was cooled to room temperature, poured into water, and extracted with toluene. The toluene layer was washed with water and dried over anhydrous sodium sulfate. Toluene was evaporated under reduced pressure. The resulting crude ether was purified by silica gel (50 g) column chromatography (developing solvent: toluene) to give 1.2 g of 3-(2-fluoroethoxy)benzyl benzyl ether.

$[n]_D^{20.4}$: 1.5508

$\nu_{max}^{film}$ (cm$^{-1}$): 2830, 1600, 1585, 1490, 1450, 1360, 1270, 1075, 1055, 890.

$\delta_{TMS}^{CCl_4}$ (ppm): 3.82–3.96 (m, 1H), 4.10–4.24 (m, 1H), 4.26–4.42 (m, 1H), 4.74–4.88 (m, 1H), 4.42 (s, 2H), 4.45 (s, 2H), 6.62–7.34 (m, 4H), 7.23 (s, 4H).

EXAMPLE 13

This example illustrates the synthesis of 3-(2-fluoroethoxy)benzyl 4-methylbenzyl ether (compound No. 96).

A mixture consisting of 1.0 g of 4-(2-fluoroethoxy)benzyl chloride, 0.65 g of 4-methylbenzyl alcohol, 0.2 g of triethylbenzylammonium chloride and 3 g of a 50% aqueous solution of sodium hydroxide was stirred at 50° C. for 3 hours. The reaction mixture was cooled to room temperature, poured into water, and extracted with benzene. The benzene layer was washed with water and dried over anhydrous sodium sulfate. Benzene was evaporated under reduced pressure. The resulting crude ether was purified by silica gel (50 g) column chromatography (developing solvent: benzene) to give 1.1 g of the desired 3-(2-fluoroethoxy)benzyl 4-methylbenzyl ether.

$[n]_D^{19.9}$: 1.5470

$\nu_{max}^{film}$ (cm$^{-1}$): 2830, 1600, 1595, 1490, 1455, 1270, 1080, 1055.

$\delta_{TMS}^{CCl_4}$ (ppm): 2.26 (s, 3H), 4.35 (s, 2H), 3.68–3.80 (m, 1H), 3.96–4.07 (m, 1H), 4.15–4.27 (m, 1H), 4.63–4.76 (m, 1H), 6.56–7.24 (m, 8H).

EXAMPLE 14

This example illustrates the synthesis of 4-(2-fluoroethoxy)benzyl 4-methoxybenzyl ether (compound No. 105).

Sodium hydride (0.32 g; 60% in oil) was suspended in 30 ml of dry acetonitrile, and 1.1 g of 4-methoxybenzyl alcohol was added. The mixture was stirred at 50° to 60° C. for 30 minutes. Then, 1.5 g of 4-(2-fluoroethoxy)benzyl chloride was added. The mixture was heated under reflux for 3 hours. The reaction mixture was cooled to room temperature, poured into water, and extracted with toluene. The toluene layer was washed with water, and dried over anhydrous sodium sulfate. Toluene was evaporated under reduced pressure. The resulting crude ether was purified by silica gel (50 g) column chromatography (developing solvent: a 9:1 mixture of benzene and ethyl acetate) to give 1.6 g of 4-(2-fluoroethoxy)benzyl 4-methoxybenzyl ether.

$[n]_D^{19.8}$: 1.5580

$\nu_{max}^{film}$ (cm$^{-1}$): 2880, 2830, 1620, 1595, 1525, 1460, 1260, 1185, 1090, 895.

$\delta_{TMS}^{CCl_4}$ (ppm): 3.56 (s, 3H), 4.38 (s, 4H), 3.78–3.90 (m, 1H), 4.05–4.16 (m, 1H), 4.24–4.35 (m, 1H), 4.70–4.82 (m, 1H), 6.52–7.22 (m, 8H).

EXAMPLE 15

Preparation of an emulsifiable concentrate:

Twenty parts (by weight; the same basis applies hereinafter) of the compound of this invention, 20 parts of SORPOL SM-100 (a registered trademark for a product of Toho Chemical Co., Ltd.; a mixture of a nonionic surfactant and an anionic surfactant) and 60 parts of xylene were mixed with stirring to form an emulsifiable concentrate.

EXAMPLE 16

Preparation of a wettable powder:

Five parts of a surfactant was added to 20 parts of the compound of this invention, and they were well stirred. Then, 75 parts of diatomaceous earth was added, and the materials were mixed with stirring in a grinder to form a wettable powder.

EXAMPLE 17

Preparation of a dust:

Three parts of the compound of this invention was dissolved in 10 parts of acetone, and 97 parts of clay adapted for use in a dust was added. Acetone was then evaporated to form a dust.

EXAMPLE 18

Preparation of granules:

Five parts of the compound of this invention, 2 parts of Serogene 7A (a trademark for carboxy methyl cellulose, a product of Daiichi Kogyo Seiyaku K.K.), 2 parts of Sun-ekisu (sodium lignosulfonate, a product of Sanyo Kokusaku Pulp K.K.)and 91 parts of clay were mixed and after addition of water, granulated. The particle size was properly arranged to form granules.

The following Test Exampls are shown to demonstrate the effectiveness of the compounds of this invention as acaricides and insecticides. In these example, the following compounds (a) to (f) were used as control compounds.

(a) DDVP[O,O-dimethyl O-(2,2-dichlorovinyl)phosphate]

(b) Diazinon[O,O-diethyl O-(2-isopropyl-6-methyl-4-pyrimidyl)phosphorothionate]

(c) Dicofol[1,1-bis(4-chlorophenyl)-2,2,2-trichloroethanol]

(d) Chlorodimeform[N'-(4-chloro-2-tolyl)-N,N-dimethylformamidine]

(e) Amitraz[3-methyl-1,5-bis(2,4-xylyl)-1,3,5-triazapenta-1,4-diene]

(f) Tetradifon[4-chlorophenyl-2',4',5'-trichlorophenylsulfone]

TEST EXAMPLE 1

In each run, an emulsifiable concentrate obtained as in Example 15 using each of the test compounds shown in Table 2 was diluted to a predetermined concentration. Fresh leaves of sweet potato were dipped in the emulsion and air-dried. The treated leaves were transferred to a plastic cup having a diameter of 10 cm and a depth of 6 cm, and 10 third-instar larvae of common cutworm (*Spodoptera litura* Fabricius) were released and allowed to eat the treated leaves of sweet potato. Seventy-two hours later, the number of dead larvae was examined. The results obtained, as the average of two replicates, are shown in Table 2.

TABLE 2

| Test compound | Insecticidal mortality (%) | |
|---|---|---|
| | 500 ppm | 100 ppm |
| Compound of the invention | | |
| No. 6 | 100 | 40 |
| No. 13 | 100 | 30 |
| No. 15 | 100 | 80 |
| No. 23 | 90 | 15 |
| No. 34 | 80 | 40 |
| No. 39 | 100 | 60 |
| No. 50 | 80 | 30 |
| No. 54 | 70 | 10 |
| No. 57 | 70 | 30 |
| No. 64 | 80 | 20 |
| No. 77 | 60 | 0 |
| No. 79 | 70 | 20 |
| No. 83 | 100 | 80 |
| No. 86 | 100 | 60 |
| No. 87 | 70 | 5 |
| No. 91 | 50 | 0 |
| No. 95 | 90 | 20 |
| No. 103 | 85 | 20 |
| No. 111 | 80 | 30 |
| Control compound (a) | 95 | 25 |

TEST EXAMPLE 2

In each run, five or six rice seedlings in the three-leaf stage were bundled and hydroponically grown in a pot with a diameter of 5 cm. Three milliliters of an acetone solution of each of the test compounds shown in Table 3 in a specified concentration was sprayed onto the rice seedlings. After air drying, the seedlings were covered with a metallic net cylinder, and twenty female imagoes of small brown planthoppers were released into the pot. The pot was then left to stand indoors at 25° C. Forty-eight hours after the treatment, the number of dead insects was examined, and the insect mortality was calculated.

The results obtained, as the average of two replicates, are shown in Table 3.

TABLE 3

| Test compound | Insecticidal mortality (%) | |
|---|---|---|
| | 100 ppm | 20 ppm |
| Compound of the invention | | |
| No. 7 | 40 | 0 |
| No. 8 | 20 | 0 |
| No. 21 | 75 | 10 |
| No. 25 | 100 | 50 |
| No. 30 | 100 | 100 |
| No. 37 | 100 | 20 |
| No. 43 | 100 | 15 |
| No. 54 | 60 | 20 |
| No. 58 | 100 | 60 |
| No. 59 | 50 | 15 |
| No. 66 | 48 | 20 |
| No. 79 | 100 | 50 |
| No. 81 | 60 | 0 |
| No. 85 | 60 | 5 |
| No. 88 | 100 | 30 |
| No. 89 | 100 | 20 |
| No. 90 | 70 | 10 |
| No. 99 | 100 | 40 |
| No. 102 | 50 | 0 |
| No. 105 | 70 | 0 |
| No. 107 | 100 | 80 |
| No. 109 | 60 | 5 |
| Control compound (b) | 100 | 80 |

TEST EXAMPLE 3

In each run, 20 female imagoes of carmine spider mites (sensitive strain) or two-spotted spider mites (sensitive strain and resistant strain) were inoculated in a kidney bean leaf disc (diameter 20 mm) placed on a wet absorbent cotton. Twenty-four hours later, an emulsifiable concentrate prepared as in Example 15 using each of the test compounds shown in Tables 4 and 5 was diluted with water to a concentration of 100 ppm, and sprayed by a spray tower having a diameter of 15 cm and a height of 50 cm so that the take-up of the chemical on the leaf disc was 1.5 mg/cm$^2$. The leaf disc was allowed to stand indoors at 25° C. for 48 hours. Then, the number of dead insects was examined, and the acarid mortality was calculated.

The results obtained, as the average of three replicates, are shown in Table 4 for the carmine spider mites, and Table 5, for the two-spotted spider mites.

TABLE 4

| Test compound | Acarid mortality (%; corrected) |
|---|---|
| Compound of the invention | |
| No. 3 | 100 |
| No. 11 | 71 |
| No. 13 | 60 |
| No. 17 | 76 |
| No. 20 | 100 |
| No. 28 | 49 |
| No. 34 | 100 |
| No. 35 | 100 |
| No. 42 | 40 |
| No. 53 | 88 |
| No. 56 | 77 |
| No. 59 | 89 |
| No. 61 | 100 |
| No. 66 | 100 |
| No. 67 | 96 |
| No. 70 | 100 |
| No. 75 | 100 |
| No. 79 | 100 |
| No. 80 | 97 |
| No. 82 | 80 |
| No. 83 | 50 |
| No. 87 | 50 |
| No. 88 | 72 |
| No. 89 | 90 |
| No. 91 | 75 |
| No. 94 | 90 |
| No. 103 | 100 |
| No. 107 | 90 |
| Control compound (c) | 100 |
| Control compound (d) | 42 |

TABLE 5

| Test compound | Acarid mortality (%; corrected) | |
|---|---|---|
| | Sensitive strain | Resistant strain |
| Compound of the invention | | |
| No. 11 | 68 | 73 |
| No. 13 | 63 | 60 |
| No. 34 | 100 | 100 |
| No. 35 | 100 | 100 |
| No. 40 | 100 | 100 |
| No. 53 | 90 | 87 |
| No. 56 | 72 | 90 |
| No. 57 | 100 | 100 |
| No. 61 | 100 | 100 |
| No. 64 | 80 | 88 |
| No. 65 | 70 | 78 |
| No. 72 | 43 | 60 |
| No. 77 | 100 | 100 |
| No. 79 | 100 | 100 |
| No. 87 | 65 | 83 |
| No. 89 | 100 | 100 |
| No. 107 | 97 | 100 |
| No. 111 | 53 | 61 |
| Control compound (a) | 97 | 0 |
| Control compound (c) | 100 | 13 |
| Control compound (e) | 100 | 67 |

TEST EXAMPLE 4

In each run, 10 to 12 female imagoes of carmine spider mites were inoculated in the same leaf disc as used in Test Example 3, and the leaf disc was left to stand indoors at 25° C. Forty-eight hours later, the imagoes were removed and the number of eggs laid was examined. Subsequently, an emulsifiable concentrate prepared as in Example 15 using each of the test compounds shown in Table 6 was diluted to a predetermined concentration, and sprayed onto the leaf disc. The number of the eggs laid on the leaf disc was about 100.

On the seventh day after the treatment, the number of surviving larvae was examined, and the hatching inhibition effect was calculated in accordance with the following equation.

$$\text{Hatching inhibition effect} = \left[1 - \frac{\text{Number of larvae surviving after 7 days}}{\text{Number of eggs laid before treatment}}\right] \times 100$$

The results obtained, as the average of three replicates, are shown in Table 6.

TABLE 6

| Test compound | Hatching inhibition effect | |
|---|---|---|
| | 50 ppm | 10 ppm |
| Compound of the invention | | |
| No. 1 | 100 | 100 |
| No. 3 | 100 | 100 |
| No. 5 | 100 | 98 |
| No. 7 | 86 | 49 |
| No. 10 | 96 | 68 |
| No. 12 | 100 | 73 |
| No. 14 | 100 | 100 |
| No. 16 | 100 | 83 |
| No. 19 | 85 | 66 |
| No. 21 | 100 | 97 |
| No. 22 | 96 | 75 |
| No. 28 | 100 | 96 |
| No. 30 | 98 | 64 |
| No. 33 | 85 | 60 |
| No. 34 | 100 | 100 |
| No. 35 | 100 | 100 |
| No. 38 | 100 | 100 |
| No. 45 | 93 | 62 |
| No. 46 | 100 | 94 |
| No. 48 | 100 | 93 |
| No. 49 | 100 | 100 |
| No. 50 | 100 | 87 |
| No. 51 | 100 | 83 |
| No. 53 | 100 | 99 |
| No. 54 | 100 | 100 |
| No. 55 | 93 | 59 |
| No. 56 | 100 | 100 |
| No. 57 | 100 | 100 |
| No. 62 | 99 | 93 |
| No. 63 | 100 | 100 |
| No. 65 | 100 | 100 |
| No. 66 | 100 | 100 |
| No. 69 | 100 | 95 |
| No. 70 | 100 | 100 |
| No. 71 | 100 | 88 |
| No. 73 | 77 | 54 |
| No. 74 | 100 | 69 |
| No. 75 | 100 | 73 |
| No. 76 | 100 | 82 |
| No. 77 | 100 | 100 |
| No. 78 | 94 | 89 |
| No. 79 | 100 | 99 |
| No. 80 | 100 | 100 |
| No. 81 | 100 | 40 |

TABLE 6-continued

| Test compound | Hatching inhibition effect | |
|---|---|---|
| | 50 ppm | 10 ppm |
| No. 83 | 74 | 38 |
| No. 84 | 100 | 91 |
| No. 85 | 100 | 78 |
| No. 86 | 97 | 64 |
| No. 87 | 100 | 100 |
| No. 88 | 100 | 100 |
| No. 89 | 100 | 100 |
| No. 90 | 100 | 100 |
| No. 91 | 100 | 100 |
| No. 92 | 100 | 100 |
| No. 93 | 100 | 100 |
| No. 96 | 100 | 58 |
| No. 97 | 100 | 100 |
| No. 98 | 100 | 86 |
| No. 100 | 100 | 100 |
| No. 101 | 100 | 97 |
| No. 104 | 100 | 100 |
| No. 106 | 77 | 43 |
| No. 107 | 100 | 100 |
| No. 109 | 100 | 100 |
| No. 110 | 100 | 91 |
| No. 111 | 100 | 100 |
| No. 112 | 98 | 91 |
| No. 115 | 100 | 95 |
| Control compound (c) | 93 | 47 |
| Control compound (f) | 100 | 71 |

TEST EXAMPLE 5

In each run, fresh leaves of "Unshu" mandarine orange were cut into square pieces each side measuring 15 mm, and placed on a wet absorbent cotton. Fifteen male imagoes of citrus red mites were inoculated and allowed to stand for 48 hours for laying eggs. Then, the imagoes were removed, and the number of eggs laid was examined. An emulsifiable concentrate prepared as in Example 15 using each of the test compounds shown in Table 7 was diluted with water to a predetermined concentration and sprayed onto the leaves. The treated leaves were left to stand indoors at 25° C. for 7 days. The number of larvae surviving on the leaves was examined, and the hatching inhibition effect was calculated as in Test Example 4.

The results obtained, as the average of three replicates, are shown in Table 7.

TABLE 7

| Test compound | Hatching inhibition effect (20 ppm) |
|---|---|
| Compound of the invention | |
| No. 1 | 100 |
| No. 3 | 95 |
| No. 8 | 100 |
| No. 9 | 93 |
| No. 17 | 100 |
| No. 19 | 89 |
| No. 22 | 85 |
| No. 31 | 100 |
| No. 34 | 100 |
| No. 35 | 100 |
| No. 36 | 82 |
| No. 37 | 98 |
| No. 48 | 100 |
| No. 50 | 100 |
| No. 52 | 98 |
| No. 55 | 78 |
| No. 56 | 100 |
| No. 58 | 100 |
| No. 59 | 100 |
| No. 60 | 100 |
| No. 61 | 92 |
| No. 68 | 100 |
| No. 72 | 98 |

TABLE 7-continued

| Test compound | Hatching inhibition effect (20 ppm) |
|---|---|
| No. 75 | 87 |
| No. 87 | 94 |
| No. 88 | 100 |
| No. 89 | 100 |
| No. 108 | 91 |
| No. 109 | 100 |
| No. 113 | 88 |
| No. 116 | 92 |
| Control compound (e) | 11 |
| Control compound (f) | 80 |

What is claimed is:

1. A 2-fluoroethoxy-substituted benzene derivative represented by the general formula

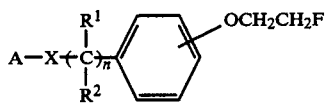
(I)

wherein X represents an oxygen or sulfur atom, $R^1$ and $R^2$ represent a hydrogen atom or a lower alkyl group, n represents 0 or 1, and A represents a group of the general formula

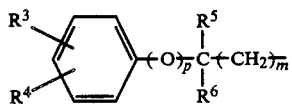
(II)

in which $R^3$ and $R^4$ represent a hydrogen atom, a halogen atom, a lower alkyl group, a lower alkoxy group, a lower alkylthio group, a lower haloalkyl group, a lower haloalkylthio group or a methylenedioxy group, $R^5$ and $R^6$ represent a hydrogen atom or a lower alkyl group, and p and m represent 0 or 1.

2. The compound of claim 1 wherein n in general formula (I) is 1, and p and m in general formula (II) are 0 and 1, respectively.

3. The compound of claim 1 wherein n in general formula (I) is 1, and p and m in general formula (II) are both 0.

4. The compound of claim 1 wherein n in general formula (I) is 0, and p and m in general formula (II) are both 0.

5. The compound of claim 1 wherein n in general formula (I) is 0, and p and m in general formula (II) are 1 and 0, respectively.

6. An insecticidal and acaricidal agent comprising a carrier and/or a surface-active agent, and as an insecticidally or acaricidally active ingredient, a 2-fluoroethoxy-substituted benzene derivative represented by the general formula

(I)

wherein X represents an oxygen or sulfur atom, $R^1$ and $R^2$ represent a hydrogen atom or a lower alkyl group, n represents 0 or 1, and A represents a group of the general formula

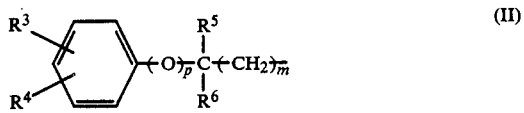
(II)

in which $R^3$ and $R^4$ represent a hydrogen atom, a halogen atom, a lower alkyl group, a lower alkoxy group, a lower alkylthio group, a lower haloalkyl group, a lower haloalkylthio group or a methylenedioxy group, $R^5$ and $R^6$ represent a hydrogen atom or a lower alkyl group, and p and m represent 0 or 1.

7. A method of combatting insect pests and/or acarids, which comprises contacting the insect pests or acarids with a pesticidally effective amount of a compound according to claim 1.

8. A method as claimed in claim 7 wherein n in general formula (I) is 1, and p and m in general (II) are 0 and 1, respectively.

9. A method as claimed in claim 7 wherein n in general formula (I) is 1, and p and m in general formula (II) are both 0.

10. A method as claimed in claim 7 wherein n in general formula (I) is 0, and p and m in general formula (II) are both 0.

11. A method as claimed in claim 7 wherein n in general formula (I) is 0, and p and m in general formula (II) are 1 and 0, respectively.

* * * * *